United States Patent
Uritski et al.

(10) Patent No.: US 10,426,828 B2
(45) Date of Patent: Oct. 1, 2019

(54) COMPOSITIONS OF MULTIMERIC-MULTIEPITOPE INFLUENZA POLYPEPTIDES AND THEIR PRODUCTION

(71) Applicant: BiondVax Pharmaceuticals Ltd., Ness Ziona (IL)

(72) Inventors: Ram Uritski, Rehovot (IL); Barry Cohen, Rehovot (IL); Zohar Gadri, Rehovot (IL); Shimon Hassin, Tel Aviv (IL)

(73) Assignee: BIONDVAX PHARMACEUTICALS LTD., Ness Ziona (IL)

( * ) Notice: Subject to any disclaimer, the term of this patent is extended or adjusted under 35 U.S.C. 154(b) by 0 days.

(21) Appl. No.: 15/300,529

(22) PCT Filed: Apr. 1, 2015

(86) PCT No.: PCT/IL2015/050354
§ 371 (c)(1),
(2) Date: Sep. 29, 2016

(87) PCT Pub. No.: WO2015/151103
PCT Pub. Date: Oct. 8, 2015

(65) Prior Publication Data
US 2017/0173142 A1    Jun. 22, 2017

Related U.S. Application Data

(60) Provisional application No. 61/974,449, filed on Apr. 3, 2014.

(51) Int. Cl.
| | | |
|---|---|---|
| *A61K 39/12* | (2006.01) | |
| *C12N 7/00* | (2006.01) | |
| *A61K 9/00* | (2006.01) | |
| *A61K 47/18* | (2017.01) | |
| *A61K 9/10* | (2006.01) | |
| *A61K 39/00* | (2006.01) | |

(52) U.S. Cl.
CPC ............ *A61K 39/12* (2013.01); *A61K 9/0019* (2013.01); *A61K 9/10* (2013.01); *A61K 47/183* (2013.01); *C12N 7/00* (2013.01); *A61K 2039/55511* (2013.01); *C12N 2760/16034* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 4,539,205 A | 9/1985 | Goodman et al. | |
| 4,643,992 A | 2/1987 | Goodman et al. | |
| 4,767,842 A | 8/1988 | Stevens | |
| 5,011,828 A | 4/1991 | Goodman et al. | |
| 5,057,540 A | 10/1991 | Kensil et al. | |
| 5,093,318 A | 3/1992 | Goodman et al. | |
| 5,709,879 A | 1/1998 | Barchfeld et al. | |
| 5,977,081 A | 11/1999 | Marciani | |
| 6,080,725 A | 6/2000 | Marciani | |
| 6,086,901 A | 7/2000 | O'Hagan et al. | |
| 6,113,918 A | 9/2000 | Johnson et al. | |
| 6,303,347 B1 | 10/2001 | Johnson et al. | |
| 6,355,257 B1 | 3/2002 | Johnson et al. | |
| 6,843,781 B2 | 1/2005 | Alchas et al. | |
| 7,250,036 B2 | 7/2007 | Alchas | |
| 8,476,053 B2 | 7/2013 | Sobek et al. | |
| 8,986,705 B2 * | 3/2015 | Trager ................ A61K 39/145 424/204.1 |
| 2003/0199441 A1 | 10/2003 | Burchardt | |
| 2004/0077540 A1 | 4/2004 | Quay | |
| 2004/0137588 A1 | 7/2004 | Scrofani et al. | |
| 2004/0265298 A1 | 12/2004 | Lin | |
| 2007/0009506 A1 | 1/2007 | Lin | |
| 2010/0152077 A1 | 6/2010 | Allston et al. | |
| 2011/0182974 A1 * | 7/2011 | Ben-Yedidia ........ A61K 39/145 424/450 |
| 2012/0134954 A1 | 5/2012 | Kwak et al. | |

FOREIGN PATENT DOCUMENTS

| | | | |
|---|---|---|---|
| EP | 0 399 843 A2 | 11/1990 | |
| GB | 2 122 204 A | 12/1985 | |
| WO | 9 517 210 A1 | 6/1995 | |
| WO | 99/56776 A2 | 11/1999 | |
| WO | 2008/025425 A1 | 3/2008 | |
| WO | 2009/015736 A1 | 2/2009 | |
| WO | 2009/016639 A2 | 2/2009 | |
| WO | 2012/054679 A1 | 4/2012 | |
| WO | 2012/114323 A1 | 8/2012 | |

OTHER PUBLICATIONS

Nayak et al. (Journal of Microencapsulation, 2009, p. 154-165).*
Morlock et al. (Eur. Journal of Pharmaceutics and Biopharmaceutics, 1997, p. 29-36).*
Ratanji et al. (Journal of Immunotoxicology, Aug. 2013, p. 99-109).*
Lyutova et al. (Biotechnology Prog. 2007, p. 1411-1416).*
Aguilar-Yáñez et al., "An Influenza A/H1N1/2009 Hemagglutinin Vaccine Produced in *Escherichia coli*," PLoS One, 5:(7), e11694, pp. 1-14 (2010).
Amon et al., "Peptide-based Synthetic Recombinant Vaccines with Anti-viral Efficacy," Biologicals, 29(3-4)237-242 (2001).
Atsmon et al., "Safety and Immunogenicity of Multimeric-001—a Novel Universal Influenza Vaccine," Journal of Clinical Immunology, 32(3):595-603 (2012).

(Continued)

*Primary Examiner* — Agnieszka Boesen
(74) *Attorney, Agent, or Firm* — J.A. Lindeman & Co., PLLC; Jeffrey Lindeman; Stephen Bellum

(57) ABSTRACT

Pharmaceutical suspensions of multimeric-multiepitope influenza polypeptides, processes for their production and their use as immunizing subjects against influenza. In particular, stable aqueous microparticulate suspensions of a multimeric multiepitope polypeptide are disclosed.

19 Claims, No Drawings
Specification includes a Sequence Listing.

(56) References Cited

OTHER PUBLICATIONS

Atsmon et al., "Priming by a novel universal influenza vaccine (Multimeric-001)—A gateway for improving immune response in the elderly population," Vaccine, 32(44):5816-5823 (2014).

Ben-Yedidia et al., "Intranasal administration of peptide vaccine protects human/mouse radiation chimera from influenza infection," International Immunology, 11(7):1043-1051 (1999).

Chiu et al., "Immunological study of HA1 domain of hemagglutinin of influenza H5N1 virus," Biochemical and Biophysical Research Communications, 383(1)27-31 (2009).

Defelippis et al., "Peptides and Proteins as Parenteral Suspensions: an Overview of Design, Development, and Manufacturing Considerations," Pharmaceutical Formulation Development of Peptides and Proteins, edited by Sven Frokjaer and Lars Hovgaard, Taylor & Francis, PA USA, 2003, Chapter 7, pp. 113-144.

Gottlieb et al., "Preparedness Ahead of Pandemic Outbreaks," BioProcess International, 11(9):20-25 (2013).

Ho et al., "The likelihood of aggregation during protein renaturation can be assessed using the second virial coefficient," Protein Science, 12(4):708-716 (2003).

Lyutova et al., "Effects of Arginine on Kinetics of Protein Aggregation Studied by Dynamic Laser Light Scattering and Tubidimetry Techniques," Biotechnology Progress (USA), 23(6):1411-1416 (2007).

Molloy et al., "Extraction of membrane proteins by differential solubilization for separation using two-dimensional gel electrophoresis," Electrophoresis, 19(5):837-844 (1998).

Nagavarma et al., "Different Techniques for Preparation of Polymeric Nanoparticles—A Review," Asian J. Pharm. Clin. Res, 5(3):16-23 (2012).

O'Hagan, et al., "Long-term antibody responses in mice following subcutaneous immunization with ovalbumin entrapped in biodegradable microparticles," Vaccine, 11(9):965-969 (1993).

Peek et al., "Nanotechnology in vaccine delivery," Advanced Drug Delivery Reviews, 60(8):915-928 (2008).

Schneider et al., "Arginine and the Hofmeister Series: The Role of Ion—Ion Interactions in Protein Aggregation Suppression," Journal of Physical Chemistry B, 115(22):7447-7458 (2011).

Suhs, "New Guanidinium Compounds for the Molecular Recognition of Carboxylates and Contributions to the Synthesis of Bivalent NPY Y1 Receptor Antagonists," Doctoral dissertation (2006).

Tsumoto et al., "Role of Arginine in Protein Refolding, Solubilization, and Purification," Biotechnology Progress, 20(5):1301-1308 (2004).

Vauthier et al., "Methods for the Preparation and Manufacture of Polymeric Nanoparticles," Pharmaceutical Research, 26(5):1025-1058 (2009).

Wingfield, "Overview of the Purification of Recombinant Proteins Produced in *Escherichia coli*," Current Protocols in Protein Science, 30:6.1:6.1.1-6.1.37 (2002).

International Search Report and Written Opinion, Appl. No. PCT/IL2015/050354, dated Jul. 21, 2015.

Hevehan et al., (1997) "Oxidative Renaturation of Lysozyme at High Concentrations," Biotechnology and Bioengineering, 54(3): 221-230.

European Search Report, Appl. No. 15773045.8, dated Aug. 21, 2017.

Rathore et al., "Refolding of biotech therapeutic proteins expressed in bacteria: review," Journal of Chemical Technology and Biotechnology, 88(10):1794-1806 (2013).

Arakawa, "Role of Arginine in Development of Biopharmaceuticals," Yakugaku Zasshi, 130(6): 793-800 (2010), English Abstract.

Shiraki, "Small Molecular Additives to Prevent Protein Inactivation and Aggregation," Seibutsu Butsuri, 44(2): 87-90 (2004), English Abstract.

\* cited by examiner

COMPOSITIONS OF MULTIMERIC-MULTIEPITOPE INFLUENZA POLYPEPTIDES AND THEIR PRODUCTION

This application is a 371 filing of International Patent Application No. PCT/IL2015/050354 filed Apr. 1, 2015, which claims the benefit of U.S. application No. 61/974,449 filed Apr. 3, 2014.

FIELD OF THE INVENTION

The present invention relates to pharmaceutical compositions of multimeric multi-epitope peptide-based influenza vaccines and to methods of their preparation. Specifically, the present invention provides microparticulate suspensions comprising a multimeric multi-epitope polypeptide and a guanidinium-containing amino acid, their preparation and their use for protecting subjects against influenza.

BACKGROUND OF THE INVENTION

Influenza is a highly infectious disease caused by rapidly mutating influenza viruses. It is easily transmitted and spreads around the world in seasonal epidemics, infecting 5-20% of the total population annually. According to the World Health Organization (WHO), 250,000-500,000 people die annually of influenza-related causes during seasonal outbreaks. In the USA alone, more than 200,000 people are hospitalized with seasonal influenza in a typical year. Influenza infection may be mild, moderate or severe, ranging from asymptomatic through mild upper respiratory infection and tracheobronchitis to a severe, occasionally lethal, viral pneumonia. The infection is associated with pulmonary and cardiovascular complications leading to high morbidity and mortality rates, affecting mainly at-risk populations such as toddlers, elderly and individuals with chronic medical conditions.

Of the three types of influenza viruses, Influenza A and Influenza B are responsible for approximately 80% and 20% of influenza disease in humans, respectively, while influenza C viruses do not infect humans. Influenza A viruses are characterized by many sub-strains and by species specificity and are considered to be the major cause of widespread seasonal epidemics and of pandemics, due to the frequent antigenic drifts and shifts of the Hemagglutinin (HA) and Neuraminidase (NA) surface proteins. Following antigenic changes, infection via virus strains which are unrecognized by the immune system may result in a reduced immune response by the infected individual, where more significant changes will yield less effective stimulation of the body's immune defenses. Antigenic drifts or shifts can trigger respective influenza epidemics or pandemics, as experienced with the recent Avian and Swine Flu pandemic strains.

To date, commercially available influenza vaccines contain influenza A and B antigens that are annually selected according to predictions of the strains to be most prevalent during the peak influenza season. However, due to the mismatch between the strains included in the vaccine and those actually circulating, these strain-specific vaccines often have relatively poor clinical efficacy. In addition, such immunization methods require preparation of new vaccine formulations on an annual basis. Thus, a vaccine recognizing multiple virus strains would be more cost effective and would further increase patient compliance and enhance global health prospects.

Commercial influenza vaccine compositions currently in use are aqueous solutions comprising typically phosphate, sodium, potassium and/or calcium buffers with additions of Triton, Tween, α-tocopheryl hydrogen succinate and/or other additives or excipients. FLUMIST™ (MedImmune), a live attenuated vaccine for influenza that presents the surface antigens of seasonal flu, is supplied as a solution comprising about 0.05 M arginine, 0.188 mg monosodium glutamate, 2 mg hydrolyzed porcine gelatin, 13.68 mg sucrose, 2.26 mg dibasic potassium phosphate, and 0.96 mg monobasic potassium phosphate.

PCT International Publication WO 2009/016639 to some of the inventors of the present invention discloses influenza multi-epitope polypeptides and vaccines comprising a plurality of influenza virus peptide epitopes wherein each epitope is present at least twice in a single polypeptide.

The Multimeric-001 (M-001) vaccine consists of nine conserved linear epitopes arranged as three repetitions of each and prepared as a single, recombinant polypeptide expressed in *Escherichia coli* (*E. coli*). These epitopes are common to the vast majority of influenza virus strains, regardless of their antigenic drifts and shifts. Consequently, M-001 is expected to provide immunity-based protection against future virus strains as well. Multimeric-001 vaccination leads to efficient cross-strain recognition and protection despite variations in the outer proteins of each strain.

The significant results obtained with various animal models and the safety parameters observed in the repeated toxicology study have paved the way toward, and provided the foundation for, clinical trials in humans. Phase I/II and Phase II clinical trials assessing the safety and immunogenicity of M-001 in adult and elderly volunteers were completed (Atsmon et al., 2014, Vaccine 32, 5816-5823). Doses of 125-500 µg adjuvanted or non-adjuvanted vaccine, in PBS, proved safe and well tolerated. Potential Multimeric-001 vaccine-related toxicity was evaluated in GLP toxicology studies. Both M-001 vaccine formulations (adjuvanted and non-adjuvanted) repeatedly IM administered at the maximal human dose, proved to be safe.

WO 2012/114323 to some of the inventors of the present invention provides a method of improving the protective effect of a seasonal or pandemic influenza vaccine by administering to a subject, prior to or together with the influenza vaccine, a multimeric influenza polypeptide comprising multiple copies of plurality of influenza virus peptide epitopes.

Formation of inclusion bodies (IBs) frequently occurs when heterologous proteins are expressed in *E. coli*, and recovery of the active recombinant protein often requires refolding into its active structure. Wingfield, P. T. (Current Protocols in Protein Science. 2003, 30:6.1.1-6.1.37) reviewed the purification of recombinant proteins produced in *E. coli*.

Arginine is used for refolding and purification of proteins obtained from IBs and appears to be effective for a variety of proteins differing in chemical and physical properties. The role of arginine in protein refolding, solubilization and purification was reviewed by Tsumoto et al., (Biotechnol Prog. 2004 September-October; 20(5): 1301-8; Schneider et al., (J Phys Chem B. 2011 Jun. 9; 115(22):7447-58)).

An anti-aggregation effect and stabilizing effect of arginine was previously described. For example, Lyutova et al., (Biotechnol Prog. 2007 November-December; 23(6):1411-6) studied the effect of low concentrations of arginine (1-10 mM) on protein aggregation, when protein aggregation is induced by transition from a folded state by heating or by addition of dithiothreitol (DTT).

Low-molecular-weight additives, such as L-arginine, have been suggested to enhance renaturation yields by inhibiting intermolecular hydrophobic interactions that lead to precipitation. Ho et al., (Protein Sci. 2003, 12, 708-716) demonstrated that L-arginine suppresses aggregation by increasing protein solubility.

Production of a protein in the form of a pharmaceutical suspension is generally favored as a result of one or more of the following reasons: the solubility of the polypeptide; the stability of the polypeptide; controlling or altering the release profile of the polypeptide.

Suspensions of protein micro- or nano-particles may be produced by a number of methods. Such particles may be initially produced as larger particles, followed by size reduction procedure by physical or chemical means. Some other approaches include crystallization, lyophilization, spray-drying and supercritical fluid particle formation or desolvation.

WO 2009/015736 discloses a process of production of a purified recombinant GDF-5 related protein comprising treatment of the inclusion bodies with a denaturing solubilization buffer comprising L-arginine.

WO 2012/054679 discloses methods for purifying a recombinant protein from a mixture comprising the recombinant protein and inclusion bodies, the method comprising: a) solubilizing the mixture comprising the recombinant protein with associated inclusion bodies with a solubilization buffer comprising ethanolamine, arginine, EDTA, urea and DTE.

US 2003/0199441 relates to a method to produce renatured procollagen propeptides wherein inclusion bodies produced in *E. coli* are dissolved in a 0.5 to 8 M denaturing buffer which is then added dropwise into a limited dilution buffer that is buffered around neutral pH and contains L-arginine in a final concentration between 200 to 1,000 nM and a disulfide bridges-reducing coupled redox system, and then the buffer mixture is dialyzed against a physiological buffer that contains L-arginine at a final concentration of 50 to 200 nM and a disulfide bridges-reducing coupled redox system and later against a physiological buffer that contains a disulfide bridges-reducing coupled redox system and finally against a physiological buffer.

US 2004/0137588 describes a method of purifying polypeptides from a biological sample subjecting the polypeptide to refolding conditions in the presence of arginine.

It would be advantageous to have stable suspensions of microparticulate polypeptides having a uniform size distribution for use in improved multimeric-multiepitope influenza vaccines. Efficient production processes of such compositions are also required.

SUMMARY OF THE INVENTION

The present invention provides improved influenza vaccine suspensions comprising at least one multimeric influenza polypeptide comprising multiple copies of a plurality of influenza virus peptide epitopes, herein denoted multimeric-multiepitope polypeptide, and a guanidinium-containing amino acid or a derivative thereof. Methods of producing such suspension compositions are also provided.

The present invention is based in part on the finding that controlled generation of protein aggregates during removal of chaotropic and reducing agents from the multimeric-multiepitope polypeptide solution, together with addition of the amino acid arginine, results in stable and uniform microparticulate suspensions of the multimeric-multiepitope polypeptide at a desired protein concentration and pH which is close to a physiological pH, overcoming the need for high pressure homogenization in order to convert large amorphous aggregates into injectable formulations.

According to one aspect, the present invention provides a pharmaceutical composition in the form of an aqueous suspension, said pharmaceutical composition comprising at least one multimeric-multiepitope polypeptide, a guanidinium-containing amino acid or a derivative thereof, and a pharmaceutically-acceptable diluent, excipient or carrier.

According to some embodiments, the pharmaceutical composition is in the form of a vaccine for immunization of a subject against influenza.

According to some embodiments, the guanidinium-containing amino acid is an arginine (Arg).

According to other embodiments, the guanidinium-containing amino acid is an arginine derivative.

Any salt or free acid of L- or D-arginine, or of a derivative thereof, or mixture thereof, can be used according to the present invention.

According to some embodiments, the arginine is L-arginine (L-Arg).

According to some embodiments, the Arg compound is selected from the group consisting of: Arg-hydrochloride, Arg-sulfate, Arg-phosphate, Arg-citrate, Arg-acetate and Arg free acid. Each possibility represents a separate embodiment of the present invention.

According to some embodiments the composition comprises L-Arg hydrochloride (L-Arg HCl).

According to some embodiments, the pharmaceutical composition comprises a guanidinium-containing amino acid or a derivative thereof in a concentration of 0.1-2.0 M.

According to some embodiments, the pharmaceutical composition comprises L-arginine in a concentration of 0.15-0.45 M. According to other embodiments, the arginine concentration in the pharmaceutical composition is 0.15-0.30 M.

According to some embodiments, the pharmaceutical composition comprises an additional buffering agent having a concentration of 1-50 mM.

According to some embodiment, the buffering agent is selected from the group consisting of: citrate buffer, tris hydroxymethylaminomethane (Tris) buffer, HEPES (4-(2-hydroxyethyl)-1-piperazineethanesulfonate) buffer, lysine buffer, glycine buffer, MOPS (3-(N-morpholino)propansulfonate) buffer, imidazole buffer and MES (2-(N-morpholino) ethanesulfonate) buffer. Each possibility represents a separate embodiment of the present invention.

According to specific embodiments, the composition comprises a buffer selected from the group consisting of: citrate buffer, lysine buffer and glycine buffer. Each possibility represents a separate embodiment of the present invention.

According to a particular embodiment, the composition comprises a citrate buffer.

According to some embodiments, the pH of the pharmaceutical composition is within the range of pH 5.0 to 7.6. According to particular embodiments, the pH of the pharmaceutical composition is within the range of pH 5.5 to 7.0. According to other particular embodiments, the buffering agent maintains a pH within the range of 5.7-6.5.

According to certain specific embodiments, a pharmaceutical composition is provided comprising 1-5 mg/ml of multimeric-multiepitope influenza polypeptide, 0.1-0.5 M of L-arginine and 10-50 mM citrate buffer, having a pH in the range of 5.0 to 7.0.

According to a specific embodiment, the pharmaceutical composition comprises 1-4 mg/ml of multimeric-multiepitope influenza polypeptide, 0.1-0.3 M L-arginine and 10-30 mM citrate buffer, having a pH in the range of 5.5 to 6.5.

According to a specific embodiment, the pharmaceutical composition comprises about 2.5 mg/ml of multimeric-multiepitope influenza polypeptide, about 0.2 M arginine, about 20 mM citrate buffer, and a pH of about 6.

According to some embodiments the pharmaceutical composition is a suspension comprising insoluble aggregates having a size distribution within the range of 0.5-50 μm wherein 95% of the aggregate sizes falling into a range of one order of magnitude.

According to some embodiments 95% of the aggregates in the suspension have a size distribution selected from the group consisting of: 0.5-5 μm, 1-10 μm, 3-30 μm and 5-50 μm. Each possibility represents a separate embodiment of the present invention.

According to some embodiments the multimeric-multiepitope influenza polypeptide is produced recombinantly.

According to some specific embodiments, the multimeric-multiepitope influenza polypeptide is denoted M-001 having an amino acid sequence as set forth in SEQ ID NO: 86.

According to another aspect, the present invention provides a process of producing a purified recombinant multimeric-multiepitope polypeptide suspension, comprising the steps:
  i. solubilizing inclusion bodies containing at least one multimeric-multiepitope polypeptide in a solution comprising a chaotropic agent, a buffering agent, and a reducing agent, having a pH in a range of 7 to 11; and
  ii. inducing controlled aggregation by gradual removal of the chaotropic and reducing agents consequently forming insoluble aggregate suspension;
  iii. addition of arginine to achieve a stable and uniform suspension having a uniform aggregate size distribution, with 95% of the aggregate sizes falling into a size range of one order of magnitude.

According to specific embodiments the chaotropic agent comprises 5-8 M urea and 1-4 M thiourea.

According to particular embodiments, gradual removal of the chaotropic and reducing agents in step (ii) is performed by ultrafiltration.

According to some embodiments, the CHAPS in step (i) is present at a concentration of 0.5-2%.

According to some embodiments, the process comprises the steps:
  i. providing E. coli cells expressing at least one multimeric-multiepitope influenza polypeptide;
  ii. performing lysis and bacterial cell disruption to provide inclusion bodies comprising multimeric-multiepitope influenza polypeptide;
  iii. solubilizing the inclusion bodies in a solution comprising 5-8M urea, 1-4 M thiourea, 0.5-4% CHAPS (3-[(3-cholamidopropyl)dimethylammonio]-1-propanesulfonate), a buffering agent, and a reducing agent, at a pH in the range of 7 to 11;
  iv. inducing controlled aggregation by gradual removal of the chaotropic and reducing agents consequently forming insoluble aggregate suspension;
  v. addition of arginine to achieve a stable and uniform suspension having a uniform aggregate size distribution, with 95% of the aggregates falling into a size range of one order of magnitude.

According to some embodiments, gradual removal of chaotropic and reducing agents is performed by ultrafiltration using a procedure known in the art.

According to some embodiments, at least one chromatography separation step is performed between steps (iii) and (iv). According to some embodiments, the at least one chromatography separation step is selected from the group consisting of ion exchange chromatography and hydrophobic interaction chromatography.

According to some embodiments, step (v) is performed prior or during to aggregate formation of step (iv).

According to yet other embodiments, step (v) is performed following aggregate formation of step (iv).

According to some embodiments, the process comprises:
  i. providing E. coli cells expressing at least one multimeric-multiepitope influenza polypeptide;
  ii. performing lysis, bacterial cell disruption and centrifugation of the E. coli cells to provide inclusion bodies comprising multimeric-multiepitope influenza polypeptide;
  iii. performing at least one wash of the inclusion bodies;
  iv. solubilizing the inclusion bodies in a solution comprising 5-8M urea, 1-4 M thiourea, 0.5-4% CHAPS (3-[(3-cholamidopropyl)dimethylammonio]-1-propanesulfonate), a reducing agent and a buffering agent providing a pH in the range of 7-10;
  v. subjecting the solution to at least one chromatography step;
  vi. inducing of controlled aggregation by gradual removal of the chaotropic and reducing agents, thereby forming insoluble aggregates;
  vii. addition of guanidinium-containing compound, and
  viii. formulating the composition of (vii) to achieve a final suspension of about 0.1-0.4 M guanidinium-containing amino acid and 10-40 mM citrate buffer, at a pH in the range of 4 to 8.

According to other embodiments the addition of guanidinium-containing compound of step (vii) is performed gradually during induction of controlled aggregation.

According to some embodiments, lysis is performed in a buffer comprising Tris buffer, EDTA, and 0.1-0.5 mg lysozyme per 1 g of cell paste at a pH in the range of 7 to 9.

According to some embodiments, inducing of controlled aggregation of step (vi) is performed by ultrafiltration.

According to some embodiments, ultrafiltration comprises the steps of:
  i. Buffer exchange I with 10-80 mM MES buffer pH 4-6.5;
  ii. Buffer exchange II with 20-80 mM citrate buffer, 0.1-1 M arginine, pH 4-6;
  iii. Buffer exchange III with 10-50 mM citrate buffer, 0.1-0.5 M arginine, pH 4.0 to 7.5.

According to other embodiments, ultrafiltration comprises the steps of:
  i. Buffer exchange I with 10-80 mM MES buffer pH 4.0 to 6.5;
  ii. Buffer exchange II with 20-80 mM citrate buffer pH 4 to 6;
  iii. Dilution with arginine containing solution to 0.1-1 M arginine concentration.

According to some embodiments, the polypeptide concentration in the final composition is 1-10 mg/ml.

According to some embodiments, the at least one multimeric-multiepitope influenza polypeptide sequence is set forth in SEQ ID NO. 86.

According to some embodiments, the at least one multimeric-multiepitope influenza polypeptide is encoded by a polynucleotide sequence set forth in SEQ ID NO. 85.

According to some specific embodiments the process comprises the steps:

i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 50 mM glycine, having a pH of about 9.5;
ii. inducing aggregation by gradual removal of the chaotropic and reducing agents (urea, thiourea and β-mercaptoethanol), thereby forming suspension of insoluble aggregates;
iii. subjecting the suspension to concentration and buffer-exchange steps by ultrafiltration comprising gradually addition of 0.5 M arginine buffer; and
iv. subjecting the suspension to buffer exchange to achieve a final composition comprising about 2.5 mg/ml of the polypeptide, about 0.2 M arginine and about 20 mM citrate buffer, having a pH about 6.

According to yet another aspect, the present invention provides a process of producing an essentially stable aqueous suspension of a recombinant multimeric-multiepitope polypeptide, comprising the steps of:
i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 5-50 mM glycine, having a pH in the range of 7 to 10;
ii. inducing aggregation by gradual removal of the chaotropic and reducing agents, thereby forming suspension of insoluble aggregates;
iii. subjecting the suspension to concentration and buffer-exchange steps by ultrafiltration comprising gradually addition of an arginine buffer or a citrate buffer; and
iv. subjecting the suspension to buffer exchange to achieve a final stable and uniform suspension comprising about 1-5 mg/ml of the polypeptide, about 0.1-0.5 M arginine and about 10-50 mM citrate buffer, having a pH in the range of 4 to 7.

According to some embodiments, the process comprises the steps:
i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 50 mM glycine having a pH of about 9.5;
ii. inducing aggregation by gradual removal of the chaotropic and reducing agents, thereby forming suspension of insoluble aggregates;
iii. subjecting the suspension to concentration and buffer-exchange steps by ultrafiltration comprising gradually addition of 0.1-1 M arginine buffer; and
iv. subjecting the suspension to buffer exchange to achieve a final suspension comprising about 1-5 mg/ml of the polypeptide, about 0.1-0.5 M arginine and about 10-50 mM citrate buffer, and having a pH in the range of 4 to 7.

According to other embodiments, a final suspension comprising about 2.5 mg/ml of the polypeptide, about 0.2 M arginine and about 20 mM citrate buffer, and having a pH of about 6 is achieved in step (iv).

According to other embodiments, the process comprises the steps of:
i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 50 mM HEPES, 5 mM glycine, and having a pH of about 8.0;
ii. inducing aggregation by gradual removal of the chaotropic and reducing agents, thereby forming suspension of insoluble aggregates;
iii. subjecting the suspension to concentration and buffer-exchange steps by ultrafiltration comprising gradually addition of 20-80 mM citrate buffer; and
iv. subjecting the suspension to dilution with arginine containing solution to achieve a final uniform microparticulate suspension comprising about 1-5 mg/ml of the polypeptide, about 0.1-0.5 M arginine and about 10-50 mM citrate buffer, and having a pH in the range of 4 to 7.

According to other embodiments, a final stable and uniform microparticulate suspension comprising about 2.5 mg/ml of the polypeptide, about 0.2 M arginine and about 20 mM citrate buffer, and having a pH about 6 is achieved in step (iv).

According to some embodiments the final microparticulate suspension comprises aggregate size distribution within the range of 0.5-50 μm wherein 95% of the aggregate sizes falling into a range of one order of magnitude.

According to some embodiments 95% of the aggregates in the final microparticulate suspension have a size distribution selected from the group consisting of 0.5-5 μm, 1-10 μm, 3-30 μm and 5-50 μm. each possibility represents a separate embodiment of the present invention.

The present invention further provides a pharmaceutical composition produced according to any of the processes herein detailed.

A multimeric polypeptide according to the present invention comprises a plurality of influenza virus peptide epitopes each epitope being present at least twice in a single polypeptide. Within the context of this invention, a "multimeric" polypeptide is a polypeptide that contains a plurality of repeats (at least two, typically at least three or more), not necessarily adjacent, of an amino acid stretch of the polypeptide. The term "multimeric multiepitope" therefore relates to a polypeptide containing a plurality of repeats of a plurality of epitopes. The multimeric multiepitope polypeptide can be produced recombinantly, as an isolated polypeptide or as a fusion protein. The polypeptide aggregates can be used on their own or mixed or formulated with an additional adjuvant.

Multimeric multiepitope polypeptides contained in the pharmaceutical and vaccine compositions of the invention contain a combination of influenza virus B-cell epitopes, T-helper epitopes, and cytotoxic lymphocyte (CTL) epitopes. The epitopes are preferably selected from conserved (non-hypervariable) regions of hemagglutinin protein (HA) peptides, matrix protein (M1 and/or M2) peptides, and nucleoprotein (NP) peptides. The epitopes preferably have a demonstrable cross-reaction activity against several human influenza subtypes and are chosen for their improved ability to induce cellular and humoral immune responses.

According to other embodiments the influenza peptide epitopes within the multimeric polypeptide contained in a composition according to the present invention are selected from the group consisting of SEQ ID NO:1 to SEQ ID NO:82. Each possibility represents a separate embodiment of the present invention.

According to some specific embodiments the influenza peptide epitopes are selected from epitopes E1-E9 (SEQ ID NOs. 82, 48, 25, 52, 51, 59, 89, 69 and 70. Each possibility represents a separate embodiment of the present invention.

According to some specific embodiments a multimeric multiepitope polypeptide comprises 3-5 repeats of 4-9 epitopes arranged in a block copolymer structure or in alternating sequential polymeric structure. Each possibility represents a separate embodiment of the present invention.

According to yet other embodiments the multimeric polypeptide sequence contained in a pharmaceutical composition according to the present invention is selected from the group consisting of: SEQ ID NO:84, SEQ ID NO:86, and SEQ ID NO:88. Each possibility represents a separate embodiment of the present invention.

The pharmaceutical composition according to the present invention can be administrated via a route selected from the group consisting of: intramuscular, intranasal, oral, intraperitoneal, subcutaneous, topical, intradermal, and transdermal delivery.

According to particular embodiments the pharmaceutical composition is administered intranasally, intramuscularly or intradermally. According to some embodiments the multimeric polypeptide contained in a pharmaceutical composition is not conjugated to and are devoid of a carrier or a fusion protein. In other embodiments a polypeptide contained in pharmaceutical compositions of the present invention may further comprise a carrier sequence, namely the peptide epitopes are inserted within a sequence of a carrier polypeptide or are coupled to a carrier sequence.

According to some embodiments the pharmaceutical compositions according to the present invention do not contain an adjuvant. According to other embodiments the vaccine further comprises a pharmaceutically acceptable adjuvant.

Pharmaceutically acceptable adjuvants include, but are not limited to water in oil emulsion, lipid emulsion, or submicron oil in water emulsion and liposomes. According to specific embodiments the adjuvant is selected from the group consisting of: Montanide™, alum, muramyl dipeptide, Gelvac®, chitin microparticles, chitosan, cholera toxin subunit B, Intralipid®, Lipofundin® or bacterial lipids, lipoproteins, and/or membrane proteins.

In some embodiments the vaccine is formulated for intramuscular, intranasal, oral, intraperitoneal, subcutaneous, topical, intradermal and transdermal delivery. In some embodiments the vaccine is administered intranasally. In other embodiments the vaccine is administered intramuscularly. In yet other embodiments the vaccine is administered intradermally.

The invention provides, according to a further aspect a method of inducing an immune response and conferring protection against influenza in a subject, comprising administering to the subject a pharmaceutical composition described above in a form of a vaccine.

Use of a vaccine composition according to the present invention, for immunization against influenza is also within the scope of the present invention. The vaccine composition according to the present invention may be administered as a stand-alone vaccine, or as part of a vaccination regiment comprising co-administration with a seasonal or pandemic influenza vaccine. Co-administration according to the present invention encompass either that both the multimeric polypeptide and the seasonal or pandemic vaccine are included in one combined composition, or that they are administered to the patient at least 24 hours apart, in two separate vaccinations.

According to some embodiments a vaccine composition comprising at least one multimeric-multiepitope influenza polypeptide is co-administered with a seasonal or pandemic influenza vaccine.

The multimeric-multiepitope polypeptides comprising a plurality of influenza virus peptide epitopes, contained in the compositions of the present invention can be produced as a recombinant protein, a fusion protein, and by chemical synthesis.

The present invention further provides pharmaceutical compositions comprising a combination of at least one multimeric influenza polypeptide and at least one conventional seasonal or pandemic influenza composition. A conventional seasonal vaccine (TIV) typically contains three inactivated or live attenuated influenza virus strains selected each year by the WHO to provide protection against the strains that are expected to infect in the coming season. A pandemic vaccine typically includes one influenza virus strain specific to the relevant strain causing the pandemic.

Further embodiments and the full scope of applicability of the present invention will become apparent from the detailed description given hereinafter. However, it should be understood that the detailed description and specific examples, while indicating particular embodiments of the invention, are given by way of illustration only, since various changes and modifications within the spirit and scope of the invention will become apparent to those skilled in the art from this detailed description.

DETAILED DESCRIPTION OF THE INVENTION

Improved pharmaceutical compositions of multimeric multiepitope polypeptide influenza vaccines, and methods for their production are herein provided. These pharmaceutical compositions have improved stability properties. While previous compositions comprising multimeric multiepitope influenza polypeptides were based on phosphate-buffer-saline, were difficult to produce and had a tendency to re-aggregate, the present invention provides stable suspension compositions comprising the amino acid Arginine or a derivative thereof, and citrate buffer and improved processes for their production.

In previously known preparation methods, a polypeptide aggregation was induced by a pH shift from basic to neutral pH, resulting in creation of large amorphous aggregates which required high pressure homogenization in order to convert them into injectable form. The present invention overcomes these limitations by controlled generation of protein aggregates during removal of chaotropic and reducing agents from the polypeptide solution, together with addition of the amino acid arginine, resulting in stable and uniform microparticulate suspension of the multimeric-multiepitope influenza polypeptide.

Multimeric Multiepitope Polypeptides

A multimeric polypeptide used in vaccines and methods according to the present invention comprises at least two repeats of each epitope. A multimeric polypeptide according to the present invention comprises according to some particular embodiments, at least three repeats of each epitope. Vaccine compositions comprising a seasonal or pandemic vaccine and at least one multimeric multiepitope polypeptide, comprising a plurality of influenza virus peptide epitopes, are also provided.

Various exemplary embodiments are provided, for multimeric vaccines comprising influenza epitopes selected from Table 1, wherein the number of repeats for each epitope is the same or different and wherein the polypeptide can be arranged in an alternating sequential polymeric structure or a block copolymer structure. The term "alternating sequential polymeric" structure means that a single copy of all the epitopes contained in the polypeptide are arranged sequentially and this arrangement is repeated sequentially a number of times equal to the number of repeats. For example, if the multimeric multiepitope polypeptide comprises four repeats of three epitopes $X_1$, $X_2$ and $X_3$ in an alternating sequential structure, the polypeptide has the following polymeric structure: $X_1X_2X_3$-$X_1X_2X_3$-$X_1X_2X_3$-$X_1X_2X_3$, also written $[X_1X_2X_3]_4$. The term "block copolymer" structure means that all the copies of a single epitope contained in the polypeptide are arranged adjacently. For example, a similar multimeric multiepitope polypeptide comprising four repeats of three epitopes $X_1$, $X_2$ and $X_3$ in a block copolymer structure has the following polymeric structure: $X_1X_1X_1X_1$-$X_2X_2X_2X_2$-$X_3X_3X_3X_3$, also written $[A]_4$-$[B]_4$-$[C]_4$.

The synthetic or recombinant influenza multi-epitope polypeptide used in pharmaceutical compositions according to the present invention is selected from the group consisting of:

i. $B(X_1ZX_2Z \ldots X_m)_nB$; and ii. $B(X_1)_nZ(X_2)_nZ \ldots (X_m)_nB$;

wherein B denotes a sequence of 0-4 amino acid residues; n is at each occurrence independently an integer of 2-50; m is an integer of 3-50; each of $X_1$, $X_2 \ldots X_m$ is an influenza peptide epitope consisting of 4-24 amino acid residues; Z at each occurrence is a bond or a spacer of 1-4 amino acid residues; and wherein the maximal number of amino acid residues in the polypeptide is about 1000. Each possibility represents a separate embodiment of the present invention.

According to some embodiments n is at each occurrence independently an integer of 2-50; m is an integer of 3-15; each of $X_1$-$X_m$ is an influenza peptide epitope selected from the group consisting of a B-cell type epitope, a T-helper (Th) type epitope, and a cytotoxic lymphocyte (CTL) type epitope, consisting of 4-24 amino acid residues. Each possibility represents a separate embodiment of the present invention.

According to yet other embodiments, n is at each occurrence independently an integer of 2-15 and m is an integer of 3-12. Each possibility represents a separate embodiment of the present invention.

According to some specific embodiments m is an integer of 4-9 and n is an integer of 3-5. Each possibility represents a separate embodiment of the present invention.

According to some specifics embodiment m is 9 and n is 3.

According to other embodiments the influenza peptide epitopes of the multimeric polypeptide contained in a pharmaceutical composition of the invention, are selected from the group consisting of a Hemagglutinin (HA) peptide, an M1 peptide, an M2 peptide, and a nucleoprotein (NP) peptide. Each possibility represents a separate embodiment of the present invention.

According to other embodiments the influenza peptide epitopes within the multimeric polypeptide contained in a composition according to the present invention are selected from the group consisting of SEQ ID NO: 1 to SEQ ID NO:82 (depicted in Table 1). Each possibility represents a separate embodiment of the present invention.

TABLE 1

| SEQ ID NO: | Amino Acid Sequence |
|---|---|
| 1 | EVET |
| 2 | MSLLTEVETHTRNGW |
| 3 | PIRNEWGCR |

TABLE 1-continued

| SEQ ID NO: | Amino Acid Sequence |
|---|---|
| 4 | ETPIRNEWGC |
| 5 | PIRNEWGCRCN |
| 6 | LLTEVETPI |
| 7 | SLLTEVETP |
| 8 | SLLTEVETPI |
| 9 | LTEVETPLT |
| 10 | MSLLTEVETPIRNEW |
| 11 | MSLLTEVETPIRNEWGCR |
| 12 | MSLLTEVETLTKNGW |
| 13 | MSLLTEVETLTRNGW |
| 14 | LTEVETPIR |
| 15 | LTEVETPIRN |
| 16 | EVETPIRNE |
| 17 | EVETPIRNEW |
| 18 | LTEVETPIRNE |
| 19 | LTEVETPIRNEWGCR |
| 20 | EVETPIRN |
| 21 | MSLLTEVETPTRNEWECR |
| 22 | SLLTEVETPTRNEWECRCSDSSD |
| 23 | SLLTEVETPIRNEWGCRCNDSSD |
| 24 | VETPIRNEW |
| 25 | SLLTEVETYVL |
| 26 | SLLTEVETYVP |
| 27 | LLTEVETYV |
| 28 | SIVPSGPL |
| 29 | SGPLKAEIAQRLEDV |
| 30 | GPLKAEIAQRLE |
| 31 | RLEDVFAGK |
| 32 | ALMEWLKTRPI |
| 33 | PILSPLTKGI |
| 34 | ILSPLTKGI |
| 35 | LTKGILGFVFTLTVPSERG |
| 36 | TKGILGFVFTLTV |
| 37 | KGILGFVFTLTV |
| 38 | GILGFVFTL |
| 39 | LGFVFTLTV |
| 40 | ILGFVFTLT |
| 41 | ASCMGLIY |
| 42 | RMGAVTTEV |

TABLE 1-continued

| SEQ ID NO: | Amino Acid Sequence |
|---|---|
| 43 | GLVCATCEQIA |
| 44 | QMVATTNPL |
| 45 | QMVATTNPLI |
| 46 | RMVLASTTAK |
| 47 | DLLENLQTY |
| 48 | SKAYSNCYPYDVPDYASL |
| 49 | SKAFSNCYPYDVPDYASL |
| 50 | STAYSNCYPYDVPDYASL |
| 51 | WTGVTQN |
| 52 | WLTGKNGLYP |
| 53 | WLTEKEGSYP |
| 54 | PKYVKQNTLKLATGMRNVP |
| 55 | GVKLESMGIYQ |
| 56 | EISGVKLESMG |
| 57 | NVKNLYEKVK |
| 58 | KVKILPKDRWTQHTTTGG |
| 59 | PKYVKQNTLKLAT |
| 60 | KTGGPIYRR |
| 61 | CTELKLSDY |
| 62 | HPSAGKDPKKTGGP |
| 63 | HPSAGKDPKKTGG |

TABLE 1-continued

| SEQ ID NO: | Amino Acid Sequence |
|---|---|
| 64 | FWRGENGRKTRSAYERMCNILKGK |
| 65 | ILRGSVAHK |
| 66 | KLLQNSQVY |
| 67 | SAAFEDLRVLSFIRG |
| 68 | SAAFEDLRVSSFIRGT |
| 69 | SAAFEDLRVLSFIRGY |
| 70 | ELRSRYWAIRTRSG |
| 71 | ELRSRYWAI |
| 72 | SRWAIRTR |
| 73 | YWAIRTRSGG |
| 74 | SRWAIRTR |
| 75 | LPFDKPTIM |
| 76 | VSDGGPNLY |
| 77 | RRSFELKKL |
| 78 | RRATAILRK |
| 79 | RPIIRPATL |
| 80 | ADRGLLRDI |
| 81 | PYYTGEHAKAIGN |
| 82 | PAKLLKERGFFGAIAGFLE |

According to some specific embodiments the influenza peptide epitopes are selected from epitopes E1-E9 (SEQ ID NOs. 82, 48, 25, 52, 51, 59, 89, 69 and 70, detailed in Table 2.

TABLE 2 influenza peptide epitopes E1 to E9

| Epitope | Epitope Type | Protein residues | Amino Acid Sequence | SEQ ID NO: |
|---|---|---|---|---|
| E1 | B cell | HA 354-372 | PAKLLKERGFFGAIAGFLE | 82 |
| E2 | B cell | HA 91-108 | SKAYSNCYPYDVPDYASL | 48 |
| E3 | B cell & CTL | M1 2-12 | SLLTEVETYVL | 25 |
| E4 | B cell | HA 150-159 | WLTGKNGLYP | 52 |
| E5 | B cell | HA 143-149 | WTGVTQN | 51 |
| E6 | T helper | NP 206-229 | FWRGENGRKTRSAYERMCNILKGK | 64 |
| E7 | T helper | HA 307-319 | PK/RYVKQNTLKLAT | 59, 89 |
| E8 | CTL | NP 335-350 | SAAFEDLRVLSFIRGY | 69 |
| E9 | CTL | NP 380-393 | ELRSRYWAIRTRSG | 70 |

It is to be noted that peptide epitopes listed herein are provided as for exemplary purposes only. The influenza virus proteins vary between isolates, thereby providing multiple variant sequences for each influenza protein. Accordingly, the present invention encompasses peptide epitopes having one or more amino acid substitutions, additions or deletions.

According to more specific embodiments the influenza peptide epitopes included in a multimeric polypeptide contained in a vaccine pharmaceutical composition according to the present invention consist of: HA 354-372 (E1, SEQ ID NO: 82), HA 91-108 (E2, SEQ ID NO: 48), M1 2-12 (E3, SEQ ID NO: 25), HA 150-159 (E4, SEQ ID NO: 52), HA 143-149 (E5, SEQ ID NO: 51), NP 206-229 (E6, SEQ ID NO: 64), HA 307-319 (E7, SEQ ID NO: 59 or 89), NP 335-350 (E8, SEQ ID NO: 69), and NP 380-393 (E9, SEQ ID NO: 70).

According to yet other embodiments the multimeric polypeptide sequence contained in a pharmaceutical composition according to the present invention is selected from the group consisting of: SEQ ID NO:84, SEQ ID NO:86, and SEQ ID NO:88. Each possibility represents a separate embodiment of the present invention.

According to yet other embodiments the multimeric polypeptide sequence contained in a pharmaceutical composition according to the present invention is encoded by a polynucleotide sequence selected from the group consisting of: SEQ ID NO:83, SEQ ID NO:85, and SEQ ID NO:87. Each possibility represents a separate embodiment of the present invention.

In some embodiments the pharmaceutical composition comprises three to five repeats of the five to nine epitopes arranged in a block copolymer structure or in alternating sequential polymeric structure. Each possibility represents a separate embodiment of the present invention.

According to s a pharmaceutical composition of the present invention comprises three repeats of nine different influenza virus peptide epitopes arranged in the following block copolymer structure [E1E1E1-E2E2E2-E3E3E3-E4E4E4-E5E5E5-E6E6E6-E7E7E7-E8E8E8-E9E9E9], wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

According to other embodiments the multimeric polypeptide comprises nine different influenza virus peptide epitopes arranged in the following alternating sequential polymeric structure [E1E2E3E4E5E6E7E8E9]$_n$, wherein n is 3 to 5; E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

According to yet other embodiments the multimeric polypeptide comprises six repeats of five different B-cell type influenza virus peptide epitopes arranged in the following alternating sequential polymeric structure [E1E2E3E4E5]$_6$, wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51).

According to other embodiments the multimeric polypeptide comprises six repeats of four different T-cell type influenza virus peptide epitopes arranged in the following alternating sequential polymeric structure [E7E8E9E6]6, wherein E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

According to additional embodiments the multimeric polypeptide comprises six repeats of nine different influenza virus peptide epitopes arranged in the following block copolymer structure [E2E2E2E2E2E2-E1E1E1E1E1E1-E3E3E3E3E3E3-E4E4E4E4E4E4-E5E5E5E5E5E5-E6E6E6E6E6E6-E7E7E7E7E7E7-E8E8E8E8E8E8-E9E9E9E9E9E9], wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

In various embodiments the multimeric polypeptide comprises at least two repeats of each epitope, typically at least three repeats of each epitope, alternatively at least four repeats, alternatively at least five repeats, alternatively at least six repeats of each epitope, maximum at least 50 repeats of each epitope. To improve the exposure of the epitopes to the immune system, the epitopes may be separated by a spacer, which according to certain embodiments consists of a single amino acid and according to other embodiments comprises 2-6 amino acids. According to some specific embodiments, the spacer consists of 1-4 neutral amino acid residues. Each possibility represents a separate embodiment of the present invention.

According to some embodiments peptide epitopes within a multimeric polypeptide contained in a pharmaceutical composition are linked by a spacer selected from the group consisting of: a bond, an amino acid, and a peptide comprising 2-6 amino acids.

According to some embodiments at least one amino acid of the spacer induces a specific conformation on a segment of the polypeptide (e.g. a proline residue).

According to yet other embodiments the spacer comprises a cleavable sequence. According to one embodiment the cleavable spacer is cleaved by intracellular enzymes. According to a more specific embodiment the cleavable spacer comprises a protease specific cleavable sequence.

Processes for Producing Suspensions
Solubilization of 'Insoluble' Inclusion Bodies Inclusion bodies of recombinant multimeric-multiepitope polypeptides formed in two different strains of *E. coli* exhibited limited solubility, probably due to hydrophobic interactions. Standard procedure of 8 M urea buffer supplemented with 50 mM βME did not solubilize the inclusion bodies at neutral pH. Addition of non-ionic or zwitterionic detergents did not improve the buffer performance. Anionic detergent addition (sodium dodecyl sulfate, SDS) enabled complete inclusion bodies solubilization, but this method is unsuitable due to SDS interference with following purification steps. Initially, basic (12) pH was used in order to solubilize the inclusion bodies in 8 M urea buffer. Later on, in was surprisingly found that a buffer regularly used for membrane protein solubilization can be modified and used for inclusion bodies solubilization at a lower pH (8-9.5). A solution comprising 6 M urea, 2 M thiourea, 1% CHAPS (3-[(3-cholamidopropyl)dimethylammonio]-1-propanesulfonate), 50 mM βME, 50 mM glycine and a pH of about 9.5 was used to achieve full solubilization of the inclusion bodies.

Ultrafiltration and Aggregate Formation

Ultrafiltration is used, according to the present invention, in the production process of the multimeric-multiepitope polypeptides, for gradual removal of chaotropic (urea and thiourea for example) and reducing (βME for example) agents, and gradual addition of arginine, for controlled creation of protein aggregates at a protein concentration of 1-50 mg/ml, suitable for use, after buffer exchange, in the final composition.

Arginine Stabilizing Effect

Arginine is not used, according to the present invention, to prevent aggregate formation as described in the art, but for size reduction and increased uniformity of protein microparticles. High concentration (about 0.2-1 M) of arginine buffer is added gradually to solubilized inclusion bodies, via an ultrafiltration buffer exchange process. The final arginine concentration of 0.1-0.5 M is achieved by further buffer exchange.

Suspension Compositions

As disclosed by Akers et al., (J. Parenteral Sci. Technol., 41, 88-96, 1987), the basic reasons for preparing pharmaceutical suspensions include the following:

1. The solubility of the peptide or protein prohibits solution formulation.

2. The stability of the peptide or protein is improved in a suspension formulation.

3. There is a desire to control or retard the release profile of the peptide or protein.

There are at least four approaches for producing particles that can be considered for development of peptide or protein suspension formulations:

1. The suspension is composed exclusively of crystalline material in vehicle.

2. The suspension is composed exclusively of amorphous material in vehicle.

3. The suspension contains a mixture of crystalline and amorphous material in vehicle.

4. The suspension contains active ingredient in both the suspension and solution phases.

There are at least four methods of producing the sterile powder: crystallization, lyophilization, spraydrying, and supercritical fluid particle formation. Given the propensity of peptides and proteins to denature under high-stress conditions, crystallization and lyophilization are more generally applicable to this class of compounds. These two methods also have proven ability to maintain the sterility of the dried material. The spray-drying process might result in denaturation either at the liquid-air interface or from the high temperature required to evaporate solvent; however, the technique may be appropriate for small peptides that lack higher-order structure.

Aqueous or non-aqueous vehicle containing any necessary excipients is prepared separately—from particle formation. Examples of non-aqueous vehicles include any highly purified natural or synthetic oil such as sesame, peanut, or other vegetable oils. Depending on the solubility of the constituents and overall viscosity of the vehicle, sterilization can be accomplished by either filtration or autoclaving. The sterile combination approach offers more flexibility in the choice of vehicle (aqueous or non-aqueous), since particle growth is accomplished independently. Once processing of each section is completed, the dry particles and vehicle are aseptically combined. Some form of agitation is required to achieve a homogeneous dispersion of particles. In the case of peptides or proteins, appropriate controls should be in place to ensure that the dispersion process does not result in denaturation or other physical changes.

The present invention provides a process of producing a purified recombinant multimeric-multiepitope polypeptide suspension, comprising the steps:
  i. solubilizing inclusion bodies containing at least one multimeric-multiepitope polypeptide in a solution comprising a chaotropic agent, a buffering agent, and a reducing agent, having a pH in a range of 7-11; and
  ii. inducing controlled aggregation by gradual removal of the chaotropic and reducing agents consequently forming insoluble aggregate suspension;
  iii. addition of arginine to achieve a stable and uniform suspension having a uniform aggregate size distribution, with 95% of the aggregate sizes falling into a size range of one order of magnitude.

According to some embodiments the pH in step (i) is in a range of 7-10.

According to some embodiments the chaotropic agent is urea, thiourea, or a combination thereof.

According to specific embodiments the chaotropic agent comprises 5-8 M urea and 1-4 M thiourea.

According to particular embodiments, gradual removal of the chaotropic and reducing agents in step (ii) is performed by ultrafiltration.

According to some embodiments, the CHAPS in step (i) is present at a concentration of 0.5-2%.

According to some embodiments, the process comprises the steps:
  i. providing *E. coli* cells expressing at least one multimeric-multiepitope influenza polypeptide;
  ii. performing lysis and bacterial cell disruption to provide inclusion bodies comprising multimeric-multiepitope influenza polypeptide;
  iii. solubilizing the inclusion bodies in a solution comprising 5-8M urea, 1-4 M thiourea, 0.5-4% CHAPS (3-[(3-cholamidopropyl)dimethylammonio]-1-propanesulfonate), a buffering agent, and a reducing agent, at a pH in the range of 7-11;
  iv. inducing controlled aggregation by gradual removal of the chaotropic and reducing agents consequently forming insoluble aggregate suspension;
  v. addition of arginine to achieve a stable and uniform suspension having a uniform aggregate size distribution, with 95% of the aggregates falling into a size range of one order of magnitude.

According to some embodiments, gradual removal of chaotropic and reducing agents is performed by ultrafiltration using a procedure known in the art.

According to some embodiments, at least one chromatography separation step is performed between steps (iii) and (iv). According to some embodiments, the at least one chromatography separation step is selected from the group consisting of ion exchange chromatography and hydrophobic interaction chromatography.

According to some embodiments, step (v) is performed prior to aggregate formation of step (iv).

According to other embodiments, step (v) is performed during aggregate formation of step (iv).

According to yet other embodiments, step (v) is performed following aggregate formation of step (iv).

According to some embodiments, the process comprises:
  i. providing *E. coli* cells expressing at least one multimeric-multiepitope influenza polypeptide;
  ii. performing lysis, bacterial cell disruption and centrifugation of the *E. coli* cells to provide inclusion bodies comprising multimeric-multiepitope influenza polypeptide;
  iii. performing at least one wash of the inclusion bodies;

iv. solubilizing the inclusion bodies in a solution comprising 5-8M urea, 1-4 M thiourea, 0.5-4% CHAPS (3-[(3-cholamidopropyl)dimethylammonio]-1-propanesulfonate), a reducing agent and a buffering agent providing a pH in the range of 7-10;
v. subjecting the solution to at least one chromatography step;
vi. inducing of controlled aggregation by gradual removal of the chaotropic and reducing agents, thereby forming insoluble aggregates;
vii. addition of guanidinium-containing compound, and
viii. formulating the composition of (vii) to achieve a final suspension of about 0.1-0.4 M guanidinium-containing amino acid and 10-40 mM citrate buffer, at a pH in the range of 4-8.

According to other embodiments the addition of guanidinium-containing compound of step (vii) is performed gradually during induction of controlled aggregation.

According to some embodiments, the bacterial cell disruption of step (ii) is performed by high pressure homogenization.

According to other embodiments, the bacterial cell disruption is performed by sonication.

According to some embodiments, lysis is performed in a buffer comprising Tris buffer, EDTA, and 0.1-0.5 mg lysozyme per 1 g of cell paste at a pH in the range of 7-9.

According to some embodiments, the urea of step (iv) is in a concentration of 6-7 M.

According to some embodiments, the buffering agent of step (iv) is HEPES in a concentration of 20-100 mM.

According to other embodiments, the buffering agent of step (iv) is glycine in a concentration of 5-100 mM.

According to some embodiments, the reducing agent of step (iv) is β-mercaptoethanol in a concentration of 20-80 mM.

According to some embodiments, inducing of controlled aggregation of step (vi) is performed by ultrafiltration.

Any ultrafiltration method known is the art is suitable for use according to the present invention, including but not limited to hollow fiber, Tangential Flow Filtration (TFF) cassette, and stirred cell.

According to some embodiments, ultrafiltration comprises the steps of:
i. Buffer exchange I with 10-80 mM MES buffer pH 4-6.5;
ii. Buffer exchange II with 20-80 mM citrate buffer, 0.1-1 M arginine, pH 4-6;
iii. Buffer exchange III with 10-50 mM citrate buffer, 0.1-0.5 M arginine, pH 4-7.5.

According to other embodiments, ultrafiltration comprises the steps of:
i. Buffer exchange I with 10-80 mM MES buffer pH 4-6.5;
ii. Buffer exchange II with 20-80 mM citrate buffer pH 4-6;
iii. Dilution with arginine containing solution to 0.1-1 M arginine concentration.

According to some embodiments, the polypeptide concentration in the final composition is 1-10 mg/ml.

According to yet other embodiments, the polypeptide concentration in the final composition is 1-4 mg/ml.

According to some embodiments, the at least one multimeric-multiepitope influenza polypeptide sequence is set forth in SEQ ID NO. 86.

According to some embodiments, the at least one multimeric-multiepitope influenza polypeptide is encoded by a polynucleotide sequence set forth in SEQ ID NO. 85.

According to some specific embodiments the process comprises the steps:

i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 50 mM glycine, having a pH of about 9.5;
ii. inducing aggregation by gradual removal of the chaotropic and reducing agents (urea, thiourea and β-mercaptoethanol), thereby forming suspension of insoluble aggregates;
iii. subjecting the suspension to concentration and buffer-exchange steps by ultrafiltration comprising gradually addition of 0.5 M arginine buffer; and
iv. subjecting the suspension to buffer exchange to achieve a final composition comprising about 2.5 mg/ml of the polypeptide, about 0.2 M arginine and about 20 mM citrate buffer, having a pH about 6.

According to yet another aspect, the present invention provides a process of producing an essentially stable aqueous suspension of a recombinant multimeric-multiepitope polypeptide, comprising the steps of:
i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 5-50 mM glycine, having a pH in the range of 7-10;
ii. inducing aggregation by gradual removal of the chaotropic and reducing agents, thereby forming suspension of insoluble aggregates;
iii. subjecting the suspension to concentration and buffer-exchange steps by ultrafiltration comprising gradually addition of an arginine buffer or a citrate buffer; and
iv. subjecting the suspension to buffer exchange to achieve a final stable and uniform suspension comprising about 1-5 mg/ml of the polypeptide, about 0.1-0.5 M arginine and about 10-50 mM citrate buffer, having a pH in the range of 4-7.

According to some embodiments, in step (i) the pH is in the range of 8-10.

According to some embodiments, the process comprises the steps:
i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 50 mM glycine having a pH of about 9.5;
ii. inducing aggregation by gradual removal of the chaotropic and reducing agents, thereby forming suspension of insoluble aggregates;
iii. subjecting the suspension to concentration and buffer-exchange steps by ultrafiltration comprising gradually addition of 0.1-1 M arginine buffer; and
iv. subjecting the suspension to buffer exchange to achieve a final suspension comprising about 1-5 mg/ml of the polypeptide, about 0.1-0.5 M arginine and about 10-50 mM citrate buffer, and having a pH in the range of 4-7.

According to some specific embodiments, in step (iii) 0.5 M arginine buffer is added;

According to other embodiments, a final suspension comprising about 2.5 mg/ml of the polypeptide, about 0.2 M arginine and about 20 mM citrate buffer, and having a pH of about 6 is achieved in step (iv).

According to other embodiments, the process comprises the steps of:
i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, 50 mM HEPES, 5 mM glycine, and having a pH of about 8.0;

ii. inducing aggregation by gradual removal of the chaotropic and reducing agents, thereby forming suspension of insoluble aggregates;

iii. subjecting the suspension to concentration and buffer-exchange steps by ultrafiltration comprising gradually addition of 20-80 mM citrate buffer; and iv. subjecting the suspension to dilution with arginine containing solution to achieve a final uniform microparticulate suspension comprising about 1-5 mg/ml of the polypeptide, about 0.1-0.5 M arginine and about 10-50 mM citrate buffer, and having a pH in the range of 4-7.

According to some specific embodiments, in step (iii) 50 mM citrate buffer is added.

According to other embodiments, a final stable and uniform microparticulate suspension comprising about 2.5 mg/ml of the polypeptide, about 0.2 M arginine and about 20 mM citrate buffer, and having a pH about 6 is achieved in step (iv).

According to some embodiments the final microparticulate suspension comprises aggregate size distribution within the range of 0.5-50 μm wherein 95% of the aggregate sizes falling into a range of one order of magnitude.

According to some embodiments 95% of the aggregates in the final microparticulate suspension have a size distribution of 0.5-5 μm.

According to some embodiments 95% of the aggregates in the final microparticulate suspension have a size distribution of 1-10 μm.

According to some embodiments 95% of the aggregates in the final microparticulate suspension have a size distribution of 3-30 μm.

According to some embodiments 95% of the aggregates in the final microparticulate suspension have a size distribution of 5-50 μm.

Definitions

For convenience, certain terms employed in the specification, examples and claims are described herein.

A multimeric-multiepitope polypeptide according to the present invention denotes a polypeptide comprising multiple copies of plurality of influenza virus peptide epitopes.

The term "immunogenicity" or "immunogenic" relates to the ability of a substance to stimulate or elicit an immune response. Immunogenicity is measured, for example, by determining the presence of antibodies specific for the substance. The presence of antibodies is detected by methods known in the art, for example using an ELISA or HAI assay.

Influenza epitopes can be classified as B-cell type, T-cell type or both B cell and T cell type, depending on the type of immune response they elicit. The definition of B cell or T cell peptide epitope is not unequivocal; for example, a peptide epitope can induce antibody production but at the same time that epitope can possess a sequence that enables binding to the human HLA molecule, rendering it accessible to CTLs or Th cells, hence a dual B cell and T cell classification for that particular epitope. "CTL", "killer T cells" or "cytotoxic T cells" is a group of differentiated T cells that recognize and lyse target cells bearing a specific foreign antigen that function in defense against viral infection and cancer cells. "T helper cell" or "Th" is any of the T cells that when stimulated by a specific antigen release cytokines that promote the activation and function of B cells and killer T cells.

"Amino acid sequence", as used herein, refers to an oligopeptide, peptide, polypeptide, or protein sequence, and fragment thereof, and to naturally occurring or synthetic molecules.

In the specification and in the claims the term "spacer" denotes any chemical compound, which may be present in the polypeptide sequence, at one of the terminals or between two epitopes. According to some embodiments, the spacer consists of 1-4 amino acid residues. The spacer may comprise a sequence that can be cleaved by enzymatic means, or may decompose spontaneously. The spacer may enforce or induce beneficial conformation to the polypeptide. The spacer may optionally comprise a protease specific cleavable sequence.

The term "insoluble," is defined herein as the characteristic of being visible to the unaided eye, when in an aqueous suspension. "Insoluble" particles can be precipitated or recovered upon centrifugation of an aqueous suspension.

The term "suspension," is defined herein as an aqueous medium that comprises an "insoluble" particle component as defined above.

The term "microparticle" is defined herein as an "insoluble" protein aggregate of 0.1-100 μm size. According to some embodiments the microparticles of the invention are within size range of 0.5-50 μm.

The term "solution," is defined herein as an aqueous medium that is substantially free of "insoluble" particles as that term is defined above.

"Uniformity" is defined herein by size distribution of aggregates as measured by a parameter which is tested for example by a LUMiSizer suspension analyzer (LUM GmbH). A uniform suspension is defined herein as having aggregate size distribution with 95% of the aggregate sizes falling into a range of one order of magnitude.

A uniform microparticulate suspension is an aqueous medium comprising "insoluble" protein aggregates (defined above as microparticles), having a uniform aggregate size distribution, with 95% of the aggregate sizes falling into a range of one order of magnitude (e.g. 0.1-1 μm, 1-10 μm, 3-30 μm, 9-90 μm etc.).

The size distribution of the particles contained in a uniform microparticulate suspension according to the present invention is narrow. The term "narrow particle size distribution" as used herein refers to a distribution wherein more than 90% of the particles have a particle size in the range of 0.2-2 times the mean (or average) particle size. Preferably, more than 95% of the particles have a particle size within this range. Even more preferably more than 99% of the particles have a particle size within this range. Thus, for a particle size of 5 μm, a narrow size distribution refers to a distribution wherein more than 90%, 95% or 99% of the particles have a particle size in the range of 1-10 μm.

The microparticles are essentially spherical or spheroidal in shape but non-spherical shapes of particles, including irregular shapes, are also possible. For spherical particles the size represents the diameter while for non-spherical particles the size represents the longest dimension of an average particle.

According to the principles of the present invention, the mean particle size as used herein refers to the average particle diameter which can be determined using techniques known to those of skill in the art including, but not limited to, sedimentation flow fractionation, photon correlation spectroscopy, light scattering, electron scattering, disk centrifugation, and the like. According to some embodiments, the aggregate size distribution is determined using a LUMi-Sizer suspension analyzer (LUM GmbH) or any corresponding equipment.

"Stability" is defined herein as the condition in which aggregate size remains uniformly distributed.

A chaotropic agent is a denaturant, namely a compound that can disrupt the hydrogen bonding network between water molecules and reduce the stability of the native state of macromolecules (e.g. proteins in the present invention) by weakening the hydrophobic effect.

A guanidinium-containing amino acid according to the present invention includes but is not limited to an arginine (Arg) amino acid or a derivative thereof. L-Arg, D-Arg or a mixture thereof can be used according to the present invention.

Any salt or free acid of L-Arg or D-Arg, or of a derivative thereof, or mixture thereof, can be used according to the present invention. This includes but is not limited to a compound selected from the group consisting of: Arg-hydrochloride, Arg-sulfate, Arg-phosphate, Arg-citrate, Arg-acetate and Arg free acid.

An Arg derivative according to the present invention, includes but is not limited to methylated arginine, substituted L-arginine, nitro-arginine, N-nitro-L-arginine methyl ester (L-NAME), N-amino-L-arginine, N-methyl-L-arginine, monomethyl-L-arginine (L-NMA), nitro-L-arginine (L-NNA), aminoguanidine, 7-nitroindazole, S-ethylisothiourea, S-methylisothiourea, S-methylthiocitriulline, S-ethylthiocitrulline, N-ethylimino-L-ornithine, ornithine and ornithine derivatives; L-canavanine; citrulline; L-2-amino-3-guanidinopropionic acid, 4-Guanidinobutyric acid; α-N-substituted L-arginine; 2-L-arginyl-1,3-benzothiazole-6-carboxylic acid; Nω-(ADP-D-ribosyl)-L-arginine; Nω-phospho-L-arginine; N2-(2-carboxyethyl)-L-arginine; N2-succinyl-L-arginine; D-nopaline; D-octopine; L-arginine amide; L-arginine hydroxamate; argpyrimidine; hydroxy-L-arginine; methyl-L-arginine; N-acyl-L-arginine; N-benzoyl-D-arginine; Nγ-Nitro-L-arginine; Peptidyl-L-arginine.

According to some embodiments, a low-cost arginine or arginine derivative is used for the compositions of the present invention, in order to achieve relatively low-priced final product.

Any vaccine against influenza can be used in conjunction with the multimeric polypeptides in methods and compositions according to the present invention. The term "vaccines against influenza" includes but is not limited to, partially or highly purified or recombinant influenza proteins, inactivated viruses or "split product" inactivated influenza vaccine products, live attenuated viruses, or particles or carriers displaying influenza epitopes, including but not limited to virus like particles (VLP) and liposomes. Influenza vaccine to be used in conjunction with the multimeric polypeptides can be seasonal, pandemic or universal vaccines.

A conventional seasonal vaccine typically contains three inactivated or live attenuated influenza virus strains and is therefore denoted also TIV (trivalent influenza vaccine). The three strains are selected each year by the WHO to provide protection against the strains that are expected to infect in the coming season.

A non-limitative list of specific seasonal vaccines that can be used according to the present invention includes: VAXI-GRIP™, AGGRIPAL™, FLUVIRIN™, FLUAD™, MUTAGRIP™, FLUZONE™, FLUZONE HD™, INFLU-VAC™, FLUARIX™, FLULAVAL™, FLUMIST™, AFLURIA™, AGRIFLU™.

A pandemic vaccine typically includes one influenza virus strain specific to the relevant strain causing the pandemic. For example, The A/H1N1 strain used for swine flu pandemic during 2009/2010 season, was then included in the later seasonal TIV formulation such as the 2010/2011 season.

According to other embodiments the pandemic vaccine is against human, swine or avian influenza strains. A non-limitative list of specific pandemic vaccines that can be used according to the present invention includes: PANENZA™, PANDEMRIX™, HUMENZA™, FOCETRIA™, CELVAPAN, CELTURA™, and FLUMIST™.

Recombinant Polypeptides

The multimeric-multiepitope polypeptides of the present invention can be prepared by expression in an expression vector per se or as a chimeric protein. The methods to produce a recombinant or chimeric protein (or polypeptide, which is interchangeably used herein), comprising one or more influenza peptide epitopes are known to those with skill in the art and are detailed, for example in WO 2009/016639. A nucleic acid sequence encoding one or more influenza peptide epitopes can be inserted into an expression vector for preparation of a polynucleotide construct for propagation and expression in host cells. A nucleic acid construct encoding a polypeptide comprising multiple repeats of several epitopes, such as a multimeric multi-epitope polypeptide, can be prepared by ligation of smaller polynucleotide constructs bearing appropriated restriction sites at their 3' and 5' ends.

Production of the Multimeric Polypeptide

Once expressed by the host cell, the multimeric polypeptide can be separated from undesired components by a number of protein purification methods. One such method is through the production of inclusion bodies, which are inactive aggregates of protein that may form when a recombinant polypeptide is expressed in a prokaryote. While the cDNA may properly code for a translatable mRNA, the protein that results may not fold correctly, or the hydrophobicity of the added peptide epitopes may cause the recombinant polypeptide to become insoluble. Inclusion bodies are easily purified by methods well known in the art. Various procedures for the purification of inclusion bodies are known in the art. In some embodiments the inclusion bodies are recovered from bacterial lysates by centrifugation and are washed with detergents and chelating agents to remove as much bacterial protein as possible from the aggregated recombinant protein. To obtain soluble protein, the washed inclusion bodies are typically dissolved in denaturing agents and the released protein is then refolded by gradual removal of the denaturing reagents by dilution or dialysis (for example, Molecular cloning: a laboratory manual, 3rd edition, Sambrook, J. and Russell, D. W., 2001; CSHL Press).

Another optional method uses a polyhistidine tag on the recombinant protein. A polyhistidine-tag consists in at least six histidine (His) residues added to a recombinant protein, often at the N- or C-terminus. Polyhistidine-tags are often used for affinity purification of polyhistidine-tagged recombinant proteins that are expressed in *E. coli* or other prokaryotic expression systems. The bacterial cells are harvested by centrifugation and the resulting cell pellet can be lysed by physical means or with detergents or enzymes such as lysozyme. The raw lysate contains at this stage the recombinant protein among several other proteins derived from the bacteria and are incubated with affinity media such as NTA-agarose, HisPur resin or Talon resin. These affinity media contain bound metal ions, either nickel or cobalt to which the polyhistidine-tag binds with micromolar affinity.

The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole. The polyhistidine tag may be subsequently removed using restriction enzymes, endoproteases or exoproteases. Kits for the purification of histidine-tagged proteins can be purchased for example from Qiagen.

Vaccine Formulation and Administration

The vaccines of the present invention comprise a multi-epitope polypeptide, and optionally, an adjuvant. The vaccine can be formulated for administration in one of many different modes. In one embodiment, the vaccine is formulated for parenteral administration. In some embodiments the vaccine is formulated for mass inoculation, for example for use with a jet-injector or a single use cartridge. According to one embodiment of the invention, the vaccine administration is intramuscular. According to another embodiment the administration is intradermal. Needles specifically designed to deposit the vaccine intradermally are known in the art as disclosed for example in U.S. Pat. Nos. 6,843,781 and 7,250,036 among others. According to other embodiments the administration is performed with a needleless injector.

According to yet another embodiment the vaccine is formulated for mucosal delivery, in particular nasal delivery (Arnon et al., Biologicals. 2001; 29(3-4):237-42; Ben-Yedidia et al., Int Immunol. 1999; 11(7):1043-51). The vaccine formulation may be applied to the lymphatic tissue of the nose in any convenient manner. However, it is preferred to apply it as a liquid stream or liquid droplets to the walls of the nasal passage. The intranasal composition can be formulated, for example, in liquid form as nose drops, spray, and aerosol or suitable for inhalation, as powder, as cream, or as emulsion and optionally provided in a vessel appropriate for distributed the polypeptide. The composition can contain a variety of additives, such as adjuvant, excipient, stabilizers, buffers, or preservatives.

The formulations of the present invention may optionally comprise a mucosal delivery-enhancing agent such as for example a permeabilizing peptide that reversibly enhances mucosal epithelial paracellular transport by modulating epithelial junctional structure and/or physiology, as described in US 2004/0077540.

In another embodiment of the invention, administration is oral and the vaccine may be presented, for example, in the form of a tablet or encased in a gelatin capsule or a microcapsule. The formulation of these modalities is general knowledge to those with skill in the art.

Liposomes provide another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 500 µm. Liposomes have been found to be effective in delivering therapeutic agents to dermal and mucosal surfaces. The average survival time or half life of the intact liposome structure can be extended with the inclusion of certain polymers, for example polyethylene glycol, allowing for prolonged release in vivo. Liposomes may be unilamellar or multilamellar.

Polymer microparticles and nanoparticles employ small biodegradable spheres which act as depots for vaccine delivery. The major advantage that polymer microspheres possess over other depot-effecting adjuvants is that they are extremely safe and have been approved for use as a biodegradable drug delivery system. The rates of copolymer hydrolysis are very well characterized, which in turn allows for the manufacture of microparticles with sustained antigen release over prolonged periods of time (O'Hagen, et al., Vaccine. 1993, 11, 965). Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 µm to 200 µm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers. In some applications an adjuvant or excipient may be included in the vaccine formulation. The choice of the adjuvant is determined in part by the mode of administration of the vaccine. For example, non-injected vaccination will lead to better overall compliance and lower overall costs. One mode of administration route is intramuscular administration. Non-limiting examples of intranasal adjuvants include chitosan powder, PLA and PLG microspheres, QS-21, calcium phosphate nanoparticles (CAP) and mCTA/LTB (mutant cholera toxin E112K with pentameric B subunit of heat labile enterotoxin).

The adjuvant used may also be, theoretically, any of the adjuvants known for peptide- or protein-based vaccines. For example: inorganic adjuvants in gel form (aluminium hydroxide/aluminium phosphate, calcium phosphate, bacterial adjuvants such as monophosphoryl lipid A and muramyl peptides, particulate adjuvants such as the so-called ISCOMS ("immunostimulatory complexes", liposomes and biodegradable microspheres, adjuvants based on oil emulsions and emulsifiers such as IFA ("Incomplete Freund's adjuvant"), SAF, saponines (such as QS-21), squalene/squalane, synthetic adjuvants such as non-ionic block copolymers, muramyl peptide analogs, synthetic lipid A, synthetic polynucleotides and polycationic adjuvants.

Another adjuvant for use with an immunogen of the present invention is an emulsion. A contemplated emulsion can be an oil-in-water emulsion or a water-in-oil emulsion. In addition to the immunogenic polypeptide, such emulsions comprise an oil phase of squalene, squalane, peanut oil or the like as are well known, and a dispersing agent. Non-ionic dispersing agents are preferred and such materials include, for example, mono- and di-$C_{12}$-$C_{24}$-fatty acid esters of sorbitan and mannide such as sorbitan mono-stearate, sorbitan mono-oleate and mannide mono-oleate.

Such emulsions are for example water-in-oil emulsions that comprise squalene, glycerol and a surfactant such as mannide mono-oleate (Arlacel™ A), optionally with squalane, emulsified with the chimer protein particles in an aqueous phase. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France). Oil-in-water emulsion adjuvants include, for example, those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. Nos. 4,539,205, 4,643,992, 5,011,828 and 5,093,318. 7-allyl-8-oxoguanosine(loxoribine) has been shown to be particularly effective in inducing an antigen-(immunogen-) specific response.

A useful adjuvant includes monophosphoryl lipid A (MPL®), 3-deacyl monophosphoryl lipid A (3D-MPL®), manufactured by Corixa Corp. The adjuvant contains three components extracted from bacteria: monophosphoryl lipid (MPL) A, trehalose dimycolate (TDM) and cell wall skeleton (CWS) (MPL+TDM+CWS) in a 2% squalene/Tween™ 80 emulsion. This adjuvant can be prepared by the methods taught in GB 2122204B.

Other compounds are structurally related to MPL® adjuvant called aminoalkyl glucosamide phosphates (AGPs) such as those available from Corixa Corp under the designation RC-529™ adjuvant (2-[(R)-3-tetra-decanoyloxytet-radecanoylamino]-ethyl-2-deoxy-4-O-phosphon-o-3-O—[(R)-3-tetradecanoyloxytetra-decanoyl]-2-[(R)-3-tetra-decanoyloxytet-radecanoyl-amino]-p-D-glucopyranoside triethylammonium salt). An RC-529 adjuvant is available in a squalene emulsion sold as RC-529SE and in an aqueous formulation as RC-529AF available from Corixa Corp. (disclosed for example in U.S. Pat. Nos. 6,355,257; 6,303, 347; and 6,113,918).

Muramyl dipeptide adjuvants are also contemplated and include N-acetyl-muramyl-L-threonyl-D-isoglutamine (thur-MDP), N-acetyl-nor-muramyl-L-alanyl-D-isoglutamine [CGP 11637, referred to as nor-MDP], and N-acetyl-muramyl-L-alanyl-D-isoglutaminyl-L-alanine-2-(1'-2'-di-palmityol-s-n-glycero-3-hydroxyphosphoryloxy) ethylamine [(CGP) 1983A, referred to as MTP-PE]. The so-called muramyl dipeptide analogues are described in U.S. Pat. No. 4,767,842.

The use of an adjuvant that contains one or more agonists for toll-like receptor-4 (TLR-4) such as an MPL® adjuvant or a structurally related compound such as an RC-529® adjuvant or a Lipid A mimetic, alone or along with an agonist for TLR-9 such as a non-methylated oligo deoxynucleotide-containing the CpG motif is also optional.

Further contemplated adjuvants include synthetic oligonucleotide adjuvants containing the CpG nucleotide motif one or more times (plus flanking sequences) available from Coley Pharmaceutical Group. The adjuvant designated QS21, available from Aquila Biopharmaceuticals, Inc., is an immunologically active saponin fractions having adjuvant activity derived from the bark of the South American tree Quillaja Saponaria Molina (e.g. Quil™ A), and the method of its production is disclosed in U.S. Pat. No. 5,057,540. Derivatives of Quil™ A, for example QS21 (an HPLC purified fraction derivative of Quil™ A also known as QA21), and other fractions such as QA17 are also disclosed. Semi-synthetic and synthetic derivatives of Quillaja Saponaria Molina saponins are also useful, such as those described in U.S. Pat. Nos. 5,977,081 and 6,080,725. The adjuvant denominated MF59 available from Chiron Corp. is described in U.S. Pat. Nos. 5,709,879 and 6,086,901.

Another type of adjuvant mixture comprises a stable water-in-oil emulsion further containing aminoalkyl glucosamine phosphates such as described in U.S. Pat. No. 6,113,918. Another water-in-oil emulsion is described in WO 99/56776.

Adjuvants are utilized in an adjuvant amount, which can vary with the adjuvant, host animal and immunogen. Typical amounts can vary from about 1 microgram to about 1 mg per immunization. Those skilled in the art know that appropriate concentrations or amounts can be readily determined.

According to some embodiments of the present invention, an adjuvant is present as a solution or emulsion which contains one or more water soluble or water-emulsifiable substances which are capable of making the vaccine isotonic or hypotonic. The water soluble or water-emulsifiable substances may be, for example, selected from the group consisting of: maltose; fructose; galactose; saccharose; sugar alcohol; lipid; and combinations thereof.

Peptide Epitopes and Analogs

The multimeric polypeptides of the present invention may be synthesized chemically using methods known in the art for synthesis of peptides, peptide multimers and polypeptides. These methods generally rely on the known principles of peptide synthesis; most conveniently, the procedures can be performed according to the known principles of solid phase peptide synthesis.

As used herein "peptide" indicates a sequence of amino acids linked by peptide bonds. The peptide epitopes according to specific embodiments of the present invention comprise a sequence of 4 to 24 amino acid residues. Multimeric polypeptides comprise at least two repeats and maximum 50 repeats of the peptide epitopes.

Peptide analogs and peptidomimetics are also included within the scope of the invention when chemical synthesis is utilized. A peptide analog according to the present invention may optionally comprise at least one non-natural amino acid and/or at least one blocking group at either the C terminus or N terminus.

The term "amino acid" refers to compounds, which have an amino group and a carboxylic acid group, preferably in a 1,2- 1,3-, or 1,4-substitution pattern on a carbon backbone. α-Amino acids are most preferred, and include the 20 natural amino acids (which are L-amino acids except for glycine) which are found in proteins. When synthesis is by chemical means the term amino acid includes also the corresponding D-amino acids of the 20 natural ones, the corresponding N-methyl amino acids, side chain modified amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, respectively, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a CHOHCH$_2$), reduced amide isosteres (a dipeptide comprising two amino acids wherein the CONH linkage is replaced by a CH$_2$NH linkage) and thioamide isosteres (a dipeptide comprising two amino acids wherein the CONH linkage is replaced by a CSNH linkage) are also useful residues for this invention.

For chemical synthesis, the amino acids used in this invention are those, which are available commercially or are available by routine synthetic methods. Certain residues may require special methods for incorporation into the peptide, and sequential, divergent or convergent synthetic approaches to the peptide sequence are useful in this invention. Natural coded amino acids and their derivatives are represented by three-letter codes according to IUPAC conventions. When there is no indication, the L isomer was used.

Conservative substitutions of amino acids as known to those skilled in the art are within the scope of the peptide epitopes of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods
Multimeric Multiepitope Polypeptides:

Multimeric-multiepitope polypeptides comprising several repeats of the influenza virus peptide epitopes E1 to E9 listed in Table 2 were produced and tested. In addition to peptide epitopes, the polypeptides include amino acids and short peptides as spacers. The polypeptides are arranged in an alternating sequential polymeric structure or a block copolymer structure. The polypeptides are prepared by expression in an expression vector from a polynucleotide construct comprising various restriction sites for further manipulation of the polypeptide. The polynucleotide construct is supplied from a commercial source.

Vaccines prepared from the multimeric-multiepitope polypeptides are used for immunization studies of various mouse models and in clinical trials in human subjects.

A multimeric polypeptide with three repeats of each of nine different epitopes arranged in block copolymer structure $[E1]_3$-$[E2]_3$-$[E3]_3$-$[E4]_3$-$[E5]_3$-$[E6]_3$-$[E7]_3$-$[E8]_3$-$[E9]_3$, was produced and denoted M-001. The estimated molecular weight of M-001 is 48 kD. The amino acid sequence of the M-001 multimeric polypeptide is set forth in SEQ ID NO: 86.

The DNA sequence of the polynucleotide construct used to prepare the M-001 multimeric peptide is set forth in SEQ ID NO: 85.

Additional multimeric-multiepitope polypeptide sequences are selected from the group consisting of: SEQ ID NO:84 and SEQ ID NO:88 encoded by polynucleotide sequences comprising a sequence selected from the group consisting of: SEQ ID NO:83 and SEQ ID NO:87 respectively.

Vaccine compositions according to the present invention may be administered without the need of an adjuvant. Alternatively, the composition may comprise an adjuvant. In such cases, optional adjuvant used in clinical trials is IFA in animal studies and Montanide™ ISA 51 VG (Seppic, France) in human trials. Montanide™ is a commonly used immune modulator that has been employed in many clinical trials testing vaccine efficacy, capable of inducing both cellular and humoral immune responses (Peek et al., Adv Drug Deliv Rev. 2008; 60, 915-928).

Example 1: Production Process of M-001—Option A

Fermentation Process:

The fermentation process was performed using heat-shock inducible *E. coli* recombinantly expressing the M-001 polypeptide. An overnight inoculum was added to 10 L bacterial growth medium. The fed-batch process was carried out at 36° C. Induction was initiated by increasing the temperature to 42° C. Two hours after induction, the batch was terminated at final volume of 15 L. The cells were then centrifuged and the recovered cell pellet stored at −70° C.

Cell Lysis, Inclusion Body Recovery and Washing:

The frozen cell pellet was thawed and dispersed in Lysis Buffer (50 mM Tris, 10 mM EDTA, lysozyme). After mixing and Ultra Turrax processing, the cells were passed through a Gaulin homogenizer (700-800 bars ×3 cycles). The lysate was diluted with 50 mM Tris, 0.1 M NaCl, 2% Triton X-100 and then diluted with 0.5 M Tris, 1 M NaCl. Finally the crude inclusion bodies (IBs) were recovered by centrifugation and then stored at −70° C.

The IBs pellet was then serially washed in 1% Triton; 50 mM HEPES, 1 M NaCl, pH 8; 5 M urea, 5 mM glycine, 1% Tween 80, pH 8 and finally with 50 mM HEPES, pH 8 and then stored at −70° C.

Inclusion Bodies Solubilization:

The washed inclusion bodies were solubilized in a buffer containing 6 M urea, 2 M thiourea, 50 mM glycine, 1% CHAPS, 50 mM 3-mercaptoethanol, pH 9.5.

Protein Purification:

Purification was carried out using an AKTApilot chromatography system (GE Healthcare). Solubilized protein was clarified by membrane filtration and first loaded on a cation exchange SP Sepharose FF column (GE Healthcare). The column was washed serially with Wash Buffer I (8 M urea, 5 mM glycine, 50 mM HEPES, 50 mM β-mercaptoethanol, pH 8), then with Wash Buffer II (8 M urea, 5 mM glycine, 50 mM HEPES, 50 mM β-mercaptoethanol, 200 mM NaCl, pH 8) and then eluted with 8 M urea, 5 mM glycine, 50 mM HEPES, 50 mM γ-mercaptoethanol, 250 mM NaCl, pH 8. The elution peak detected at 280 nm absorption, was collected.

The elute was then diluted with 1 M ammonium sulfate to 0.5 M ammonium sulfate, then loaded onto a second chromatography column, an hydrophobic interaction Phenyl Sepharose FF (HS) resin (GE Healthcare). The column was washed with 8 M urea, 5 mM glycine, 50 mM HEPES, 50 mM β-mercaptoethanol, 0.5 M ammonium sulfate, pH 8 and then eluted with 8 M urea, 5 mM glycine, 50 mM HEPES, 50 mM β-mercaptoethanol, pH 8. The elute was then passed through a Sartobind STIC (Sartorius) filter for the reduction of DNA and endotoxins. Tween-80 was added at a ratio of 1:5 (w/w) Tween 80: recombinant protein. The protein solution was aseptically filtered (0.2 μm). All subsequent steps were handled aseptically.

Ultrafiltration and Formulation:

The elute was concentrated using a hollow fiber module with a 10 kDa cut off (GE Healthcare). In order to form protein microparticles having controlled size distribution, the buffer was serially exchanged to 50 mM MES buffer, pH 5.5, then to 50 mM citrate buffer, 0.5 M arginine, pH 5.5 and finally to 20 mM citrate buffer, 0.2 M arginine, pH 6 which represents the Drug Substance. The pharmaceutical composition—the Drug Product, is obtained by diluting the drug substance to a protein concentration of 2.5 mg/mL in 20 mM Citrate Buffer, 0.2 M arginine, pH 6. The filled vials are stored at +4° C.

Example 2: Production Process of M-001—Option B

Fermentation Process:
Same as in Example 1.
Cell Lysis, Inclusion Body Recovery and Washing:
Same as in Example 1.
Inclusion Bodies Solubilization:
The washed inclusion bodies were solubilized in a buffer containing 6 M urea, 2 M thiourea, 5 mM glycine, 1% CHAPS, 50 mM HEPES, 50 mM β-mercaptoethanol, pH 8.0.
Protein Purification:
Purification was carried out using an AKTApilot chromatography system (GE Healthcare). Solubilized protein was clarified by membrane filtration and loaded on a cation exchange SP Sepharose FF column (GE Healthcare). The column was washed serially with Wash Buffer I (8 M urea, 5 mM glycine, 50 mM HEPES, 50 mM β-mercaptoethanol, pH 8), then with Wash Buffer II (8 M urea, 5 mM glycine, 50 mM HEPES, 50 mM β-mercaptoethanol, 200 mM NaCl, pH 8) and then eluted with 8 M urea, 5 mM glycine, 50 mM HEPES, 50 mM β-mercaptoethanol, 250 mM NaCl, pH 8. The elution peak detected at 280 nm absorption was collected.

Tween-80 was added at a ratio of 1:5 (w/w) Tween 80: recombinant protein. The protein solution was aseptically filtered (0.2 μm). All subsequent steps were handled aseptically.

Ultrafiltration and Formulation:
The elute was concentrated using a hollow fiber module with a 10 kDa cut off (GE Healthcare). In order to form controlled microparticles (i.e., controlled protein aggregates), the buffer was serially exchanged to 50 mM MES buffer, pH 5.5, then to 50 mM citrate buffer, pH 5.5, which represents the Drug Substance. Arginine solution was added to a final arginine concentration of 0.5 M. The pharmaceutical composition—the Drug Product, was obtained by diluting the drug substance to a protein concentration of 2.5 mg/mL in 50 mM citrate buffer, 0.5 M arginine, pH 5.5. The filled vials were stored at +4° C.

Example 3: Production Process of M-001 Testing PBS as the Drug Substance Buffer

Fermentation Process:
Same as in Example 1.
Cell Lysis, Inclusion Body Recovery and Washing:
Same as in Example 1.
Inclusion Bodies Solubilization:
Same as in Example 2.
Protein Purification:
Same as in Example 2.
Ultrafiltration and Formulation:
The elute was diluted 1:40 with 50 mM MES buffer, pH 5.5. The resulting solution was concentrated using a hollow fiber module with a 10 kDa cut off (GE Healthcare). In order to create protein microparticles, the buffer was exchanged to PBS buffer, pH 7.0. The appearance of the protein suspension was inferior compared to the suspension obtained in Examples 1 & 2, as visually assessed by increased flocculation and precipitation. Arginine HCl was added to final arginine concentration of 0.1-1.5 M. Arginine addition caused an immediate particle deflocculation in a dose dependent manner, higher arginine concentration created more pronounced effect.

What is claimed is:

1. An injectable pharmaceutical composition in the form of an aqueous suspension of microparticles, said composition comprising at least one multimeric-multiepitope polypeptide comprising multiple copies of plurality of influenza virus peptide epitopes, a guanidinium-containing amino acid or a derivative thereof, and a pharmaceutically-acceptable diluent, excipient or carrier, wherein the aqueous suspension comprises aggregates of microparticles of said multimeric-multiepitope polypeptide having uniform aggregate size distribution with 95% of the aggregates in the suspension having a size range distribution selected from the group consisting of: 0.5-5 μm, 0.6-6 μm, 0.7-7 μm, 0.8-8 μm, 0.9-9 μm, 1-10 μm, 2-20 μm, 3-30 μm, 4-40 μm and 5-50 μm.

2. The pharmaceutical composition of claim 1 wherein 95% of the aggregates in the suspension have a size range distribution of 1-10 μm.

3. The pharmaceutical composition according to claim 1 wherein the guanidinium-containing amino acid is an arginine (Arg).

4. The pharmaceutical composition according to claim 1 wherein the guanidinium-containing amino acid or derivative is at a concentration of 0.1-2.0 M.

5. The pharmaceutical composition according to claim 1 wherein the composition comprises a buffering agent at a concentration of 1-50 mM that maintains a pH within the range of 5.0 to 7.6.

6. The pharmaceutical composition according to claim 1 comprising 1-10 mg/ml of multimeric-multiepitope influenza polypeptide, 0.1-0.5 M of L-arginine and 10-50 mM citrate buffer, and having a pH in the range of 4 to 7.

7. The pharmaceutical composition according to claim 1 wherein the multimeric-multiepitope polypeptide comprises 3-5 repeats of 4-9 peptide epitopes each epitope is selected from the group consisting of: HA 354-372 (E1, SEQ ID NO: 82), HA 91-108 (E2, SEQ ID NO: 48), M1 2-12 (E3, SEQ ID NO: 25), HA 150-159 (E4, SEQ ID NO: 52), HA 143-149 (E5, SEQ ID NO: 51), NP 206-229 (E6, SEQ ID NO: 64), HA 307-319 (E7, SEQ ID NO: 59 or 89), NP 335-350 (E8, SEQ ID NO: 69), and NP 380-393 (E9, SEQ ID NO: 70).

8. The pharmaceutical composition according to claim 7 wherein the multimeric-multiepitope influenza polypeptide is M-001 having an amino acid sequence set forth in SEQ ID NO: 86.

9. The pharmaceutical composition of claim 1, wherein the polypeptide is a purified recombinant polypeptide produced by a process comprising the steps of:

i. providing at least one multimeric multiepitope influenza polypeptide at a concentration of 1.5-5 mg/ml in an aqueous solution comprising a chaotropic agent, a detergent, a reducing agent, and a buffering agent providing a pH in the range of 7-10;

ii. inducing of controlled aggregation by gradual removal of the chaotropic and reducing agents; and iii. adding a guanidinium-containing compound to achieve a stable microparticulate suspension having a uniform aggregate size distribution, with 95% of the aggregate sizes falling into a size range of one order of magnitude.

10. The pharmaceutical composition of claim 9 wherein the chaotropic agent is 5-8 M urea and 1-4 M thiourea, the detergent is 0.5-4% CHAPS (3-[(3-cholamidopropyl) dimethylammonio]-1-propanesulfonate) and the buffering agent is 5-100 mM glycine.

11. The pharmaceutical composition according to claim 9 further comprising the steps of:

i. providing *E. coli* cells expressing at least one multimeric-multiepitope influenza polypeptide;

ii. performing lysis, bacterial cell disruption and centrifugation of the *E. coli* cells to provide inclusion bodies comprising multimeric-multiepitope polypeptide;

iii. performing at least one wash of the inclusion bodies.

12. The pharmaceutical composition according to claim 11 comprising the steps of:

iv. solubilizing the inclusion bodies in a solution comprising a 5-8M urea, 1-4 M thiourea, 0.5-4% CHAPS, a reducing agent, and 5-100 mM glycine as a buffering agent providing a pH in the range of 7-10;

v. inducing of controlled aggregation by gradual removal of the chaotropic and reducing agents together with addition of guanidinium-containing buffer, thereby forming suspension of insoluble aggregates; and vi. formulating the suspension by means of buffer exchange to achieve a final suspension of about 0.1-0.4 M guanidinium-containing amino acid and 10-40 mM citrate buffer, having a pH in the range of 4-8.

13. The pharmaceutical composition according to claim 12 wherein at least one chromatography separation step is performed between steps (iv) and (v).

14. The pharmaceutical composition according to claim 12 wherein inducing of controlled aggregation in step (iv) is performed by ultrafiltration.

15. The pharmaceutical composition according to claim 12 wherein the polypeptide concentration in the final composition is 1-10 mg/ml.

16. The pharmaceutical composition according to claim 12 wherein the at least one multimeric-multiepitope influenza polypeptide sequence is set forth in SEQ ID NO. 86.

17. The pharmaceutical composition according to claim 12 comprising the steps of:
   i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, and 50 mM glycine providing a pH of about 9.5;
   ii. inducing aggregation by gradual removal of the chaotropic and reducing agents, thereby forming suspension of insoluble aggregates;
   iii. subjecting the suspension to concentration and buffer-exchange steps by ultrafiltration comprising gradually addition of 0.5 M arginine buffer; and
   iv. subjecting the suspension to buffer exchange to achieve a final composition comprising about 2.5 mg/ml of the polypeptide, about 0.2 M arginine and about 20 mM citrate buffer, having a pH of about 6.

18. The pharmaceutical composition of claim 1 wherein the aqueous suspension of a recombinant multimeric-multiepitope polypeptide is prepared by the steps of:
   i. solubilizing inclusion bodies comprising recombinantly-produced multimeric-multiepitope influenza polypeptide in a solution comprising 6 M urea, 2 M thiourea, 1% CHAPS, 50 mM β-mercaptoethanol, and 50 mM glycine providing a pH of about 9.5;
   ii. inducing aggregation by gradual removal of the urea, thiourea and β-mercaptoethanol, thereby forming suspension of insoluble aggregates;
   iii. subjecting the suspension to concentration and buffer-exchange steps by ultrafiltration comprising gradually addition of 0.1-1 M arginine buffer; and
   iv. subjecting the suspension to buffer exchange to achieve a final suspension comprising about 1-5 mg/ml of the polypeptide, about 0.1-0.5 M arginine and about 10-50 mM citrate buffer, having a pH in the range of 4-7.

19. A method of inducing an immune response and conferring protection against influenza in a subject, comprising administering to the subject a pharmaceutical composition according to claim 1 in form of an injectable vaccine.

* * * * *

SEQUENCE LISTING

<160> NUMBER OF SEQ ID NOS: 89

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Glu Val Glu Thr
1

<210> SEQ ID NO 2
<211> LENGTH: 15
<212> TYPE: PRT
<213> ORGANISM: Artificial
<220> FEATURE:
<223> OTHER INFORMATION: Synthetic peptide

<400> SEQUENCE: 2

Met Ser Leu Leu Thr Glu Val Glu Thr His Thr Arg Asn Gly Trp
1               5                   10                  15

<210> SEQ ID NO 3
<211> LENGTH: 9

```
<212> TYPE: PRT
<213> ORGANISM: Artificial
<220> FEATURE:
<223> OTHER INFORMATION: Synthetic peptide

<400> SEQUENCE: 3

Pro Ile Arg Asn Glu Trp Gly Cys Arg
1               5

<210> SEQ ID NO 4
<211> LENGTH: 10
<212> TYPE: PRT
<213> ORGANISM: Artificial
<220> FEATURE:
<223> OTHER INFORMATION: Synthetic peptide

<400> SEQUENCE: 4

Glu Thr Pro Ile Arg Asn Glu Trp Gly Cys
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic peptide

<400> SEQUENCE: 5

Pro Ile Arg Asn Glu Trp Gly Cys Arg Cys Asn
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic peptide

<400> SEQUENCE: 6

Leu Leu Thr Glu Val Glu Thr Pro Ile
1               5

<210> SEQ ID NO 7
<211> LENGTH: 9
<212> TYPE: PRT
<213> ORGANISM: Artificial
<220> FEATURE:
<223> OTHER INFORMATION: Synthetic peptide

<400> SEQUENCE: 7

Ser Leu Leu Thr Glu Val Glu Thr Pro
1               5

<210> SEQ ID NO 8
<211> LENGTH: 10
<212> TYPE: PRT
<213> ORGANISM: Artificial
<220> FEATURE:
<223> OTHER INFORMATION: Synthetic peptide

<400> SEQUENCE: 8

Ser Leu Leu Thr Glu Val Glu Thr Pro Ile
1               5                   10

<210> SEQ ID NO 9
<211> LENGTH: 9
<212> TYPE: PRT
```

```
<213> ORGANISM: Artificial
<220> FEATURE:
<223> OTHER INFORMATION: Synthetic peptide

<400> SEQUENCE: 9

Leu Thr Glu Val Glu Thr Pro Leu Thr
1               5

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Met Ser Leu Leu Thr Glu Val Glu Thr Pro Ile Arg Asn Glu Trp
1               5                   10                  15

<210> SEQ ID NO 11
<211> LENGTH: 18
<212> TYPE: PRT
<213> ORGANISM: Artificial
<220> FEATURE:
<223> OTHER INFORMATION: Synthetic peptide

<400> SEQUENCE: 11

Met Ser Leu Leu Thr Glu Val Glu Thr Pro Ile Arg Asn Glu Trp Gly
1               5                   10                  15

Cys Arg

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Met Ser Leu Leu Thr Glu Val Glu Thr Leu Thr Lys Asn Gly Trp
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Met Ser Leu Leu Thr Glu Val Glu Thr Leu Thr Arg Asn Gly Trp
1               5                   10                  15

<210> SEQ ID NO 14
<211> LENGTH: 9
<212> TYPE: PRT
<213> ORGANISM: Artificial
<220> FEATURE:
<223> OTHER INFORMATION: Synthetic peptide

<400> SEQUENCE: 14

Leu Thr Glu Val Glu Thr Pro Ile Arg
1               5

<210> SEQ ID NO 15
<211> LENGTH: 10
```

<212> TYPE: PRT
<213> ORGANISM: Artificial
<220> FEATURE:
<223> OTHER INFORMATION: Synthetic peptide

<400> SEQUENCE: 15

Leu Thr Glu Val Glu Thr Pro Ile Arg Asn
1               5                   10

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

Glu Val Glu Thr Pro Ile Arg Asn Glu
1               5

<210> SEQ ID NO 17
<211> LENGTH: 10
<212> TYPE: PRT
<213> ORGANISM: Artificial
<220> FEATURE:
<223> OTHER INFORMATION: Synthetic peptide

<400> SEQUENCE: 17

Glu Val Glu Thr Pro Ile Arg Asn Glu Trp
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic peptide

<400> SEQUENCE: 18

Leu Thr Glu Val Glu Thr Pro Ile Arg Asn Glu
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Leu Thr Glu Val Glu Thr Pro Ile Arg Asn Glu Trp Gly Cys Arg
1               5                   10                  15

<210> SEQ ID NO 20
<211> LENGTH: 8
<212> TYPE: PRT
<213> ORGANISM: Artificial
<220> FEATURE:
<223> OTHER INFORMATION: Synthetic peptide

<400> SEQUENCE: 20

Glu Val Glu Thr Pro Ile Arg Asn
1               5

<210> SEQ ID NO 21
<211> LENGTH: 18
<212> TYPE: PRT

<213> ORGANISM: Artificial
<220> FEATURE:
<223> OTHER INFORMATION: Synthetic peptide

<400> SEQUENCE: 21

Met Ser Leu Leu Thr Glu Val Glu Thr Pro Thr Arg Asn Glu Trp Glu
1               5                   10                  15

Cys Arg

<210> SEQ ID NO 22
<211> LENGTH: 23
<212> TYPE: PRT
<213> ORGANISM: Artificial
<220> FEATURE:
<223> OTHER INFORMATION: Synthetic peptide

<400> SEQUENCE: 22

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 23
<211> LENGTH: 23
<212> TYPE: PRT
<213> ORGANISM: Artificial
<220> FEATURE:
<223> OTHER INFORMATION: Synthetic peptide

<400> SEQUENCE: 23

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 24
<211> LENGTH: 9
<212> TYPE: PRT
<213> ORGANISM: Artificial
<220> FEATURE:
<223> OTHER INFORMATION: Synthetic peptide

<400> SEQUENCE: 24

Val Glu Thr Pro Ile Arg Asn Glu Trp
1               5

<210> SEQ ID NO 25
<211> LENGTH: 11
<212> TYPE: PRT
<213> ORGANISM: Artificial
<220> FEATURE:
<223> OTHER INFORMATION: Synthetic peptide

<400> SEQUENCE: 25

Ser Leu Leu Thr Glu Val Glu Thr Tyr Val Leu
1               5                   10

<210> SEQ ID NO 26
<211> LENGTH: 11
<212> TYPE: PRT
<213> ORGANISM: Artificial
<220> FEATURE:
<223> OTHER INFORMATION: Synthetic peptide

<400> SEQUENCE: 26

Ser Leu Leu Thr Glu Val Glu Thr Tyr Val Pro
1               5                   10

<210> SEQ ID NO 27
<211> LENGTH: 9
<212> TYPE: PRT
<213> ORGANISM: Artificial
<220> FEATURE:
<223> OTHER INFORMATION: Synthetic peptide

<400> SEQUENCE: 27

Leu Leu Thr Glu Val Glu Thr Tyr Val
1               5

<210> SEQ ID NO 28
<211> LENGTH: 8
<212> TYPE: PRT
<213> ORGANISM: Artificial
<220> FEATURE:
<223> OTHER INFORMATION: Synthetic peptide

<400> SEQUENCE: 28

Ser Ile Val Pro Ser Gly Pro Leu
1               5

<210> SEQ ID NO 29
<211> LENGTH: 15
<212> TYPE: PRT
<213> ORGANISM: Artificial
<220> FEATURE:
<223> OTHER INFORMATION: Synthetic peptide

<400> SEQUENCE: 29

Ser Gly Pro Leu Lys Ala Glu Ile Ala Gln Arg Leu Glu Asp Val
1               5                   10                  15

<210> SEQ ID NO 30
<211> LENGTH: 12
<212> TYPE: PRT
<213> ORGANISM: Artificial
<220> FEATURE:
<223> OTHER INFORMATION: Synthetic peptide

<400> SEQUENCE: 30

Gly Pro Leu Lys Ala Glu Ile Ala Gln Arg Leu Glu
1               5                   10

<210> SEQ ID NO 31
<211> LENGTH: 9
<212> TYPE: PRT
<213> ORGANISM: Artificial
<220> FEATURE:
<223> OTHER INFORMATION: Synthetic peptide

<400> SEQUENCE: 31

Arg Leu Glu Asp Val Phe Ala Gly Lys
1               5

<210> SEQ ID NO 32
<211> LENGTH: 11
<212> TYPE: PRT
<213> ORGANISM: Artificial
<220> FEATURE:
<223> OTHER INFORMATION: Synthetic peptide

<400> SEQUENCE: 32

Ala Leu Met Glu Trp Leu Lys Thr Arg Pro Ile

```
1               5                   10
```

<210> SEQ ID NO 33
<211> LENGTH: 10
<212> TYPE: PRT
<213> ORGANISM: Artificial
<220> FEATURE:
<223> OTHER INFORMATION: Synthetic peptide

<400> SEQUENCE: 33

```
Pro Ile Leu Ser Pro Leu Thr Lys Gly Ile
1               5                   10
```

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

```
Ile Leu Ser Pro Leu Thr Lys Gly Ile
1               5
```

<210> SEQ ID NO 35
<211> LENGTH: 19
<212> TYPE: PRT
<213> ORGANISM: Artificial
<220> FEATURE:
<223> OTHER INFORMATION: Synthetic peptide

<400> SEQUENCE: 35

```
Leu Thr Lys Gly Ile Leu Gly Phe Val Phe Thr Leu Thr Val Pro Ser
1               5                   10                  15

Glu Arg Gly
```

<210> SEQ ID NO 36
<211> LENGTH: 13
<212> TYPE: PRT
<213> ORGANISM: Artificial
<220> FEATURE:
<223> OTHER INFORMATION: Synthetic peptide

<400> SEQUENCE: 36

```
Thr Lys Gly Ile Leu Gly Phe Val Phe Thr Leu Thr Val
1               5                   10
```

<210> SEQ ID NO 37
<211> LENGTH: 12
<212> TYPE: PRT
<213> ORGANISM: Artificial
<220> FEATURE:
<223> OTHER INFORMATION: Synthetic peptide

<400> SEQUENCE: 37

```
Lys Gly Ile Leu Gly Phe Val Phe Thr Leu Thr Val
1               5                   10
```

<210> SEQ ID NO 38
<211> LENGTH: 9
<212> TYPE: PRT
<213> ORGANISM: Artificial
<220> FEATURE:
<223> OTHER INFORMATION: Synthetic peptide

<400> SEQUENCE: 38

```
Gly Ile Leu Gly Phe Val Phe Thr Leu
1               5

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39

Leu Gly Phe Val Phe Thr Leu Thr Val
1               5

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

Ile Leu Gly Phe Val Phe Thr Leu Thr
1               5

<210> SEQ ID NO 41
<211> LENGTH: 8
<212> TYPE: PRT
<213> ORGANISM: Artificial
<220> FEATURE:
<223> OTHER INFORMATION: Synthetic peptide

<400> SEQUENCE: 41

Ala Ser Cys Met Gly Leu Ile Tyr
1               5

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

Arg Met Gly Ala Val Thr Thr Glu Val
1               5

<210> SEQ ID NO 43
<211> LENGTH: 11
<212> TYPE: PRT
<213> ORGANISM: Artificial
<220> FEATURE:
<223> OTHER INFORMATION: Synthetic peptide

<400> SEQUENCE: 43

Gly Leu Val Cys Ala Thr Cys Glu Gln Ile Ala
1               5                   10

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

Gln Met Val Ala Thr Thr Asn Pro Leu
```

```
1               5

<210> SEQ ID NO 45
<211> LENGTH: 10
<212> TYPE: PRT
<213> ORGANISM: Artificial
<220> FEATURE:
<223> OTHER INFORMATION: Synthetic peptide

<400> SEQUENCE: 45

Gln Met Val Ala Thr Thr Asn Pro Leu Ile
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic peptide

<400> SEQUENCE: 46

Arg Met Val Leu Ala Ser Thr Thr Ala Lys
1               5                   10

<210> SEQ ID NO 47
<211> LENGTH: 9
<212> TYPE: PRT
<213> ORGANISM: Artificial
<220> FEATURE:
<223> OTHER INFORMATION: Synthetic peptide

<400> SEQUENCE: 47

Asp Leu Leu Glu Asn Leu Gln Thr Tyr
1               5

<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Ser Lys Ala Tyr Ser Asn Cys Tyr Pro Tyr Asp Val Pro Asp Tyr Ala
1               5                   10                  15

Ser Leu

<210> SEQ ID NO 49
<211> LENGTH: 18
<212> TYPE: PRT
<213> ORGANISM: Artificial
<220> FEATURE:
<223> OTHER INFORMATION: Synthetic peptide

<400> SEQUENCE: 49

Ser Lys Ala Phe Ser Asn Cys Tyr Pro Tyr Asp Val Pro Asp Tyr Ala
1               5                   10                  15

Ser Leu

<210> SEQ ID NO 50
<211> LENGTH: 18
<212> TYPE: PRT
<213> ORGANISM: Artificial
<220> FEATURE:
<223> OTHER INFORMATION: Synthetic peptide
```

```
<400> SEQUENCE: 50

Ser Thr Ala Tyr Ser Asn Cys Tyr Pro Tyr Asp Val Pro Asp Tyr Ala
1               5                   10                  15

Ser Leu

<210> SEQ ID NO 51
<211> LENGTH: 7
<212> TYPE: PRT
<213> ORGANISM: Artificial
<220> FEATURE:
<223> OTHER INFORMATION: Synthetic peptide

<400> SEQUENCE: 51

Trp Thr Gly Val Thr Gln Asn
1               5

<210> SEQ ID NO 52
<211> LENGTH: 10
<212> TYPE: PRT
<213> ORGANISM: Artificial
<220> FEATURE:
<223> OTHER INFORMATION: Synthetic peptide

<400> SEQUENCE: 52

Trp Leu Thr Gly Lys Asn Gly Leu Tyr Pro
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic peptide

<400> SEQUENCE: 53

Trp Leu Thr Glu Lys Glu Gly Ser Tyr Pro
1               5                   10

<210> SEQ ID NO 54
<211> LENGTH: 19
<212> TYPE: PRT
<213> ORGANISM: Artificial
<220> FEATURE:
<223> OTHER INFORMATION: Synthetic peptide

<400> SEQUENCE: 54

Pro Lys Tyr Val Lys Gln Asn Thr Leu Lys Leu Ala Thr Gly Met Arg
1               5                   10                  15

Asn Val Pro

<210> SEQ ID NO 55
<211> LENGTH: 11
<212> TYPE: PRT
<213> ORGANISM: Artificial
<220> FEATURE:
<223> OTHER INFORMATION: Synthetic peptide

<400> SEQUENCE: 55

Gly Val Lys Leu Glu Ser Met Gly Ile Tyr Gln
1               5                   10

<210> SEQ ID NO 56
<211> LENGTH: 11
<212> TYPE: PRT
<213> ORGANISM: Artificial
```

```
<220> FEATURE:
<223> OTHER INFORMATION: Synthetic peptide

<400> SEQUENCE: 56

Glu Ile Ser Gly Val Lys Leu Glu Ser Met Gly
1               5                   10

<210> SEQ ID NO 57
<211> LENGTH: 10
<212> TYPE: PRT
<213> ORGANISM: Artificial
<220> FEATURE:
<223> OTHER INFORMATION: Synthetic peptide

<400> SEQUENCE: 57

Asn Val Lys Asn Leu Tyr Glu Lys Val Lys
1               5                   10

<210> SEQ ID NO 58
<211> LENGTH: 18
<212> TYPE: PRT
<213> ORGANISM: Artificial
<220> FEATURE:
<223> OTHER INFORMATION: Synthetic peptide

<400> SEQUENCE: 58

Lys Val Lys Ile Leu Pro Lys Asp Arg Trp Thr Gln His Thr Thr Thr
1               5                   10                  15

Gly Gly

<210> SEQ ID NO 59
<211> LENGTH: 13
<212> TYPE: PRT
<213> ORGANISM: Artificial
<220> FEATURE:
<223> OTHER INFORMATION: Synthetic peptide

<400> SEQUENCE: 59

Pro Lys Tyr Val Lys Gln Asn Thr Leu Lys Leu Ala Thr
1               5                   10

<210> SEQ ID NO 60
<211> LENGTH: 9
<212> TYPE: PRT
<213> ORGANISM: Artificial
<220> FEATURE:
<223> OTHER INFORMATION: Synthetic peptide

<400> SEQUENCE: 60

Lys Thr Gly Gly Pro Ile Tyr Arg Arg
1               5

<210> SEQ ID NO 61
<211> LENGTH: 9
<212> TYPE: PRT
<213> ORGANISM: Artificial
<220> FEATURE:
<223> OTHER INFORMATION: Synthetic peptide

<400> SEQUENCE: 61

Cys Thr Glu Leu Lys Leu Ser Asp Tyr
1               5

<210> SEQ ID NO 62
<211> LENGTH: 14
<212> TYPE: PRT
```

<213> ORGANISM: Artificial
<220> FEATURE:
<223> OTHER INFORMATION: Synthetic peptide

<400> SEQUENCE: 62

His Pro Ser Ala Gly Lys Asp Pro Lys Lys Thr Gly Gly Pro
1               5                   10

<210> SEQ ID NO 63
<211> LENGTH: 13
<212> TYPE: PRT
<213> ORGANISM: Artificial
<220> FEATURE:
<223> OTHER INFORMATION: Synthetic peptide

<400> SEQUENCE: 63

His Pro Ser Ala Gly Lys Asp Pro Lys Lys Thr Gly Gly
1               5                   10

<210> SEQ ID NO 64
<211> LENGTH: 24
<212> TYPE: PRT
<213> ORGANISM: Artificial
<220> FEATURE:
<223> OTHER INFORMATION: Synthetic peptide

<400> SEQUENCE: 64

Phe Trp Arg Gly Glu Asn Gly Arg Lys Thr Arg Ser Ala Tyr Glu Arg
1               5                   10                  15

Met Cys Asn Ile Leu Lys Gly Lys
            20

<210> SEQ ID NO 65
<211> LENGTH: 9
<212> TYPE: PRT
<213> ORGANISM: Artificial
<220> FEATURE:
<223> OTHER INFORMATION: Synthetic peptide

<400> SEQUENCE: 65

Ile Leu Arg Gly Ser Val Ala His Lys
1               5

<210> SEQ ID NO 66
<211> LENGTH: 9
<212> TYPE: PRT
<213> ORGANISM: Artificial
<220> FEATURE:
<223> OTHER INFORMATION: Synthetic peptide

<400> SEQUENCE: 66

Lys Leu Leu Gln Asn Ser Gln Val Tyr
1               5

<210> SEQ ID NO 67
<211> LENGTH: 15
<212> TYPE: PRT
<213> ORGANISM: Artificial
<220> FEATURE:
<223> OTHER INFORMATION: Synthetic peptide

<400> SEQUENCE: 67

Ser Ala Ala Phe Glu Asp Leu Arg Val Leu Ser Phe Ile Arg Gly
1               5                   10                  15

<210> SEQ ID NO 68

```
<211> LENGTH: 16
<212> TYPE: PRT
<213> ORGANISM: Artificial
<220> FEATURE:
<223> OTHER INFORMATION: Synthetic peptide

<400> SEQUENCE: 68

Ser Ala Ala Phe Glu Asp Leu Arg Val Ser Ser Phe Ile Arg Gly Thr
1               5                   10                  15

<210> SEQ ID NO 69
<211> LENGTH: 16
<212> TYPE: PRT
<213> ORGANISM: Artificial
<220> FEATURE:
<223> OTHER INFORMATION: Synthetic peptide

<400> SEQUENCE: 69

Ser Ala Ala Phe Glu Asp Leu Arg Val Leu Ser Phe Ile Arg Gly Tyr
1               5                   10                  15

<210> SEQ ID NO 70
<211> LENGTH: 14
<212> TYPE: PRT
<213> ORGANISM: Artificial
<220> FEATURE:
<223> OTHER INFORMATION: Synthetic peptide

<400> SEQUENCE: 70

Glu Leu Arg Ser Arg Tyr Trp Ala Ile Arg Thr Arg Ser Gly
1               5                   10

<210> SEQ ID NO 71
<211> LENGTH: 9
<212> TYPE: PRT
<213> ORGANISM: Artificial
<220> FEATURE:
<223> OTHER INFORMATION: Synthetic peptide

<400> SEQUENCE: 71

Glu Leu Arg Ser Arg Tyr Trp Ala Ile
1               5

<210> SEQ ID NO 72
<211> LENGTH: 9
<212> TYPE: PRT
<213> ORGANISM: Artificial
<220> FEATURE:
<223> OTHER INFORMATION: Synthetic peptide

<400> SEQUENCE: 72

Ser Arg Tyr Trp Ala Ile Arg Thr Arg
1               5

<210> SEQ ID NO 73
<211> LENGTH: 10
<212> TYPE: PRT
<213> ORGANISM: Artificial
<220> FEATURE:
<223> OTHER INFORMATION: Synthetic peptide

<400> SEQUENCE: 73

Tyr Trp Ala Ile Arg Thr Arg Ser Gly Gly
1               5                   10

<210> SEQ ID NO 74
<211> LENGTH: 9
```

```
<212> TYPE: PRT
<213> ORGANISM: Artificial
<220> FEATURE:
<223> OTHER INFORMATION: Synthetic peptide

<400> SEQUENCE: 74

Ser Arg Tyr Trp Ala Ile Arg Thr Arg
1               5

<210> SEQ ID NO 75
<211> LENGTH: 9
<212> TYPE: PRT
<213> ORGANISM: Artificial
<220> FEATURE:
<223> OTHER INFORMATION: Synthetic peptide

<400> SEQUENCE: 75

Leu Pro Phe Asp Lys Pro Thr Ile Met
1               5

<210> SEQ ID NO 76
<211> LENGTH: 9
<212> TYPE: PRT
<213> ORGANISM: Artificial
<220> FEATURE:
<223> OTHER INFORMATION: Synthetic peptide

<400> SEQUENCE: 76

Val Ser Asp Gly Gly Pro Asn Leu Tyr
1               5

<210> SEQ ID NO 77
<211> LENGTH: 9
<212> TYPE: PRT
<213> ORGANISM: Artificial
<220> FEATURE:
<223> OTHER INFORMATION: Synthetic peptide

<400> SEQUENCE: 77

Arg Arg Ser Phe Glu Leu Lys Lys Leu
1               5

<210> SEQ ID NO 78
<211> LENGTH: 9
<212> TYPE: PRT
<213> ORGANISM: Artificial
<220> FEATURE:
<223> OTHER INFORMATION: Synthetic peptide

<400> SEQUENCE: 78

Arg Arg Ala Thr Ala Ile Leu Arg Lys
1               5

<210> SEQ ID NO 79
<211> LENGTH: 9
<212> TYPE: PRT
<213> ORGANISM: Artificial
<220> FEATURE:
<223> OTHER INFORMATION: Synthetic peptide

<400> SEQUENCE: 79

Arg Pro Ile Ile Arg Pro Ala Thr Leu
1               5

<210> SEQ ID NO 80
<211> LENGTH: 9
<212> TYPE: PRT
```

```
<213> ORGANISM: Artificial
<220> FEATURE:
<223> OTHER INFORMATION: Synthetic peptide

<400> SEQUENCE: 80

Ala Asp Arg Gly Leu Leu Arg Asp Ile
1               5

<210> SEQ ID NO 81
<211> LENGTH: 13
<212> TYPE: PRT
<213> ORGANISM: Artificial
<220> FEATURE:
<223> OTHER INFORMATION: Synthetic peptide

<400> SEQUENCE: 81

Pro Tyr Tyr Thr Gly Glu His Ala Lys Ala Ile Gly Asn
1               5                   10

<210> SEQ ID NO 82
<211> LENGTH: 19
<212> TYPE: PRT
<213> ORGANISM: Artificial
<220> FEATURE:
<223> OTHER INFORMATION: Synthetic peptide

<400> SEQUENCE: 82

Pro Ala Lys Leu Leu Lys Glu Arg Gly Phe Phe Gly Ala Ile Ala Gly
1               5                   10                  15

Phe Leu Glu

<210> SEQ ID NO 83
<211> LENGTH: 2199
<212> TYPE: DNA
<213> ORGANISM: Artificial
<220> FEATURE:
<223> OTHER INFORMATION: Synthetic polynucleotide

<400> SEQUENCE: 83
atgcatatga gatctccagc taaacttctg aaagaacgtg gatttttcgg tgcaatcgct      60
ggttttctgg aggggtcgaa agcctacagt aactgttacc cctacgatgt gcccgattat     120
gccagcctgg gtagcctcct tacagaagtt gaaacttatg tgctcggctg gctgacaggg     180
aaaaacggcc tttatcctgt gtggaccggc gtgacgcaga acggattctg cgtggcgaa      240 aatggacgta aaactcgcag tgcgtatgag cgcatgtgta acatcctcaa aggtaaaggc     300
ccgaaatatg tgaaacagaa tacattaaaa ttagccaccg gcgcgagcgc tgcctttgaa     360
gacctccgtg tgctcagttt tatccgcggt tatggggaac tgcgttctcg ctattgggcg     420
atccgtaccc ggtcagggg tccaccggcg aagctgctga agaacgtgg gttcttcggt      480 gcgattgccg gtttcttgga aggatcaaaa gcgtattcga actgctaccc gtatgatgtg     540
ccagattacg ccagcctggg ctccctcttg acagaggtcg aaacctatgt actgggttgg     600
ctgaccggta agaacggtct gtatccggtt tggactggtg tgacacaaaa cggcttttgg     660 cgggggggaaa acggccggaa aacccgcagc gcttacgagc gcatgtgcaa cattctgaaa     720
ggcaaaggcc cgaaatacgt gaagcagaat acgctcaaac ttgccacggg cgcaagcgca     780
gcctttgaag acctgcgggt cttgagcttt atccgcggtt acggggagct gcggtcgcgc     840
tactgggcga ttcgtacgcg tagtggtgga cctcccgcga acttctgaa agagcgggc     900 ttctttggag cgattgcggg cttcttggag ggaagcaaag cctactctaa ttgttaccca     960
```

```
tacgatgtgc ctgattatgc gagcctcggt agcttgctga cagaagtgga aacctacgtt    1020
ctcggctggc tgacgggcaa aaatggtctc tacccagtgt ggaccggagt acccagaat     1080 gggttctggc gcggtgagaa cggccgtaaa acacgttcag cgtacgagcg atgtgcaac    1140 atcttaaaag gcaaaggacc gaaatacgtc aagcagaata ctctgaagtt agccactggg    1200
gcctcagccg cctttgaaga ccttcgcgtc ttgagtttta tccggggtta tggggaactg    1260
cggagccgct actgggctat tcgtacgcgg tcgggtggcc cactcgagcc ggccaaattg    1320
ctcaaagaac gtggtttctt cggagcgatc gcaggttttc ttgaaggctc taaagcgtac    1380
agcaactgtt atccatacga tgtgccggat tacgccagtc tgggttccct cctgaccgag    1440
gtggaaacgt atgtactagg atggctcacg ggtaaaaatg gtctctatcc tgtgtggacg    1500
ggcgtaaccc agaacggctt ttggcggggc gaaaacggcc gcaaaacccg tagcgcatac    1560
gagcgtatgt gtaacatcct taaggcaaa ggtccaaaat acgttaagca gaatacctg     1620 aaactggcta cgggcgccag tgcggccttc gaagatttac gggtgctgtc cttcatccgc    1680
ggctatggtg aactgcgctc tcgttactgg gcaatccgta cccgcagtgg cggacctccg    1740
gctaaactgt tgaaagaacg cggcttcttt ggtgctatcg caggttttct ggaaggaagt    1800
aaagcatatt cgaattgtta tccctacgac gtgccggatt atgcgtcgct cggttcgctg    1860
ctgaccgagg tggaaaccta cgttctaggc tggttgacag gtaagaacgg gctttacccg    1920
gtatggaccg gcgttaccca gaacggtttt tggcgcggtg aaaatggccg taaaactcgg    1980
tcagcatacg aacggatgtg caatatcttg aaaggtaaag gaccgaaata cgttaaacag    2040
aacacgctga actggcaac aggcgccagc gcggcgtttg aggatttacg cgtcctgtca    2100
tttattcggg gctacggcga attacgtagt cgttattggg cgattcgtac ccgcagcgga    2160
gggctcgagt aataaaagct ttctagacat atgatgcat                          2199
```

<210> SEQ ID NO 84
<211> LENGTH: 723
<212> TYPE: PRT
<213> ORGANISM: Artificial
<220> FEATURE:
<223> OTHER INFORMATION: Synthetic polypeptide

<400> SEQUENCE: 84

```
Met His Met Arg Ser Pro Ala Lys Leu Leu Lys Glu Arg Gly Phe Phe
1               5                   10                  15

Gly Ala Ile Ala Gly Phe Leu Glu Gly Ser Lys Ala Tyr Ser Asn Cys
            20                  25                  30

Tyr Pro Tyr Asp Val Pro Asp Tyr Ala Ser Leu Gly Ser Leu Leu Thr
        35                  40                  45

Glu Val Glu Thr Tyr Val Leu Gly Trp Leu Thr Gly Lys Asn Gly Leu
    50                  55                  60

Tyr Pro Val Trp Thr Gly Val Thr Gln Asn Gly Phe Trp Arg Gly Glu
65                  70                  75                  80

Asn Gly Arg Lys Thr Arg Ser Ala Tyr Glu Arg Met Cys Asn Ile Leu
                85                  90                  95

Lys Gly Lys Gly Pro Lys Tyr Val Lys Gln Asn Thr Leu Lys Leu Ala
            100                 105                 110

Thr Gly Ala Ser Ala Ala Phe Glu Asp Leu Arg Val Leu Ser Phe Ile
        115                 120                 125

Arg Gly Tyr Gly Glu Leu Arg Ser Arg Tyr Trp Ala Ile Arg Thr Arg
    130                 135                 140
```

Ser Gly Gly Pro Pro Ala Lys Leu Leu Lys Glu Arg Gly Phe Phe Gly
145                 150                 155                 160

Ala Ile Ala Gly Phe Leu Glu Gly Ser Lys Ala Tyr Ser Asn Cys Tyr
                165                 170                 175

Pro Tyr Asp Val Pro Asp Tyr Ala Ser Leu Gly Ser Leu Leu Thr Glu
                180                 185                 190

Val Glu Thr Tyr Val Leu Gly Trp Leu Thr Gly Lys Asn Gly Leu Tyr
            195                 200                 205

Pro Val Trp Thr Gly Val Thr Gln Asn Gly Phe Trp Arg Gly Glu Asn
        210                 215                 220

Gly Arg Lys Thr Arg Ser Ala Tyr Glu Arg Met Cys Asn Ile Leu Lys
225                 230                 235                 240

Gly Lys Gly Pro Lys Tyr Val Lys Gln Asn Thr Leu Lys Leu Ala Thr
                245                 250                 255

Gly Ala Ser Ala Ala Phe Glu Asp Leu Arg Val Leu Ser Phe Ile Arg
                260                 265                 270

Gly Tyr Gly Glu Leu Arg Ser Arg Tyr Trp Ala Ile Arg Thr Arg Ser
            275                 280                 285

Gly Gly Pro Pro Ala Lys Leu Leu Lys Glu Arg Gly Phe Phe Gly Ala
        290                 295                 300

Ile Ala Gly Phe Leu Glu Gly Ser Lys Ala Tyr Ser Asn Cys Tyr Pro
305                 310                 315                 320

Tyr Asp Val Pro Asp Tyr Ala Ser Leu Gly Ser Leu Leu Thr Glu Val
                325                 330                 335

Glu Thr Tyr Val Leu Gly Trp Leu Thr Gly Lys Asn Gly Leu Tyr Pro
                340                 345                 350

Val Trp Thr Gly Val Thr Gln Asn Gly Phe Trp Arg Gly Glu Asn Gly
            355                 360                 365

Arg Lys Thr Arg Ser Ala Tyr Glu Arg Met Cys Asn Ile Leu Lys Gly
        370                 375                 380

Lys Gly Pro Lys Tyr Val Lys Gln Asn Thr Leu Lys Leu Ala Thr Gly
385                 390                 395                 400

Ala Ser Ala Ala Phe Glu Asp Leu Arg Val Leu Ser Phe Ile Arg Gly
                405                 410                 415

Tyr Gly Glu Leu Arg Ser Arg Tyr Trp Ala Ile Arg Thr Arg Ser Gly
                420                 425                 430

Gly Pro Leu Glu Pro Ala Lys Leu Leu Lys Glu Arg Gly Phe Phe Gly
            435                 440                 445

Ala Ile Ala Gly Phe Leu Glu Gly Ser Lys Ala Tyr Ser Asn Cys Tyr
        450                 455                 460

Pro Tyr Asp Val Pro Asp Tyr Ala Ser Leu Gly Ser Leu Leu Thr Glu
465                 470                 475                 480

Val Glu Thr Tyr Val Leu Gly Trp Leu Thr Gly Lys Asn Gly Leu Tyr
                485                 490                 495

Pro Val Trp Thr Gly Val Thr Gln Asn Gly Phe Trp Arg Gly Glu Asn
                500                 505                 510

Gly Arg Lys Thr Arg Ser Ala Tyr Glu Arg Met Cys Asn Ile Leu Lys
            515                 520                 525

Gly Lys Gly Pro Lys Tyr Val Lys Gln Asn Thr Leu Lys Leu Ala Thr
        530                 535                 540

Gly Ala Ser Ala Ala Phe Glu Asp Leu Arg Val Leu Ser Phe Ile Arg
545                 550                 555                 560

Gly Tyr Gly Glu Leu Arg Ser Arg Tyr Trp Ala Ile Arg Thr Arg Ser

```
                    565                 570                 575
Gly Gly Pro Pro Ala Lys Leu Leu Lys Glu Arg Gly Phe Phe Gly Ala
                580                 585                 590

Ile Ala Gly Phe Leu Glu Gly Ser Lys Ala Tyr Ser Asn Cys Tyr Pro
            595                 600                 605

Tyr Asp Val Pro Asp Tyr Ala Ser Leu Gly Ser Leu Leu Thr Glu Val
        610                 615                 620

Glu Thr Tyr Val Leu Gly Trp Leu Thr Gly Lys Asn Gly Leu Tyr Pro
625                 630                 635                 640

Val Trp Thr Gly Val Thr Gln Asn Gly Phe Trp Arg Gly Glu Asn Gly
                645                 650                 655

Arg Lys Thr Arg Ser Ala Tyr Glu Arg Met Cys Asn Ile Leu Lys Gly
                660                 665                 670

Lys Gly Pro Lys Tyr Val Lys Gln Asn Thr Leu Lys Leu Ala Thr Gly
            675                 680                 685

Ala Ser Ala Ala Phe Glu Asp Leu Arg Val Leu Ser Phe Ile Arg Gly
        690                 695                 700

Tyr Gly Glu Leu Arg Ser Arg Tyr Trp Ala Ile Arg Thr Arg Ser Gly
705                 710                 715                 720

Gly Leu Glu

<210> SEQ ID NO 85
<211> LENGTH: 1299
<212> TYPE: DNA
<213> ORGANISM: Artificial
<220> FEATURE:
<223> OTHER INFORMATION: Synthetic polynucleotide

<400> SEQUENCE: 85
atgcatatga gatctccagc taaacttctg aaagaacgtg attttttcgg tgcaatcgct    60
ggttttctgg agccaccggc gaagctgctg aagaacgtgg gttcttcgg tgcgattgcc   120 ggtttcttgg aacctcccgc gaaacttctg aaagagcggg gcttctttgg agcgattgcg   180
ggcttcttgg agccatcgaa agcctacagt aactgttacc cctacgatgt gcccgattat   240
gccagcctgc cttcaaaagc gtattcgaac tgctacccgt atgatgtgcc agattacgcc   300
agcctgccaa gcaaagccta ctctaattgt tacccatacg atgtgcctga ttatgcgagc   360
ctccctagcc tccttacaga agttgaaact tatgtgctca gcttgctgac agaagtggaa   420
acctacgttc tcagcttgct gacagaagtg gaaacctacg ttctctggct gacagggaaa   480 aacggcttt atccttggct gaccggtaag acggtctgt atccgtggct gacgggcaaa   540
aatggtctct acccatggac cggcgtgacg cagaacccct ggactggtgt gacacaaaac   600
ccatggaccg gagttaccca gaatcctttc tggcgtggcg aaaatggacg taaaactcgc   660
agtgcgtatg agcgcatgtg taacatcctc aaaggtaaac ccttttggcg ggggaaaac   720 ggccggaaaa cccgcagcgc ttacgagcgc atgtgcaaca ttctgaaagg caaaccattc   780
tggcgcggtg agaacggccg taaaacacgt tcagcgtacg agcggatgtg caacatctta   840
aaaggcaaac tccgaaata cgtgaagcag atacgctca aacttgccac gccaccgaaa   900
tacgtcaagc agaatactct gaagttagcc actccgccga atacgtcaa gcagaatact   960 ctgaagttag ccactccttc agccgccttt gaagaccttc gcgtcttgag ttttatccgg  1020
ggttatccaa gcgcagcctt tgaagacctg cgggtcttga gctttatccg cggttaccct  1080
tcagccgcct ttgaagacct tcgcgtcttg agttttatcc ggggttatcc agaactgcgt  1140
```

```
tctcgctatt gggcgatccg tacccggtca gggccggagc tgcggtcgcg ctactgggcg    1200
attcgtacgc gtagtggtcc agaactgcgg agccgctact gggctattcg tacgcggtcg    1260
ggttaataac tcgagaggct ttctagacat atgatgcat                           1299
```

<210> SEQ ID NO 86
<211> LENGTH: 421
<212> TYPE: PRT
<213> ORGANISM: Artificial
<220> FEATURE:
<223> OTHER INFORMATION: Synthetic polypeptide

<400> SEQUENCE: 86

```
Met His Met Arg Ser Pro Ala Lys Leu Leu Lys Glu Arg Gly Phe Phe
1               5                   10                  15

Gly Ala Ile Ala Gly Phe Leu Glu Pro Pro Ala Lys Leu Leu Lys Glu
            20                  25                  30

Arg Gly Phe Phe Gly Ala Ile Ala Gly Phe Leu Glu Pro Pro Ala Lys
        35                  40                  45

Leu Leu Lys Glu Arg Gly Phe Phe Gly Ala Ile Ala Gly Phe Leu Glu
    50                  55                  60

Pro Ser Lys Ala Tyr Ser Asn Cys Tyr Pro Tyr Asp Val Pro Asp Tyr
65                  70                  75                  80

Ala Ser Leu Pro Ser Lys Ala Tyr Ser Asn Cys Tyr Pro Tyr Asp Val
                85                  90                  95

Pro Asp Tyr Ala Ser Leu Pro Ser Lys Ala Tyr Ser Asn Cys Tyr Pro
            100                 105                 110

Tyr Asp Val Pro Asp Tyr Ala Ser Leu Pro Ser Leu Leu Thr Glu Val
        115                 120                 125

Glu Thr Tyr Val Leu Ser Leu Leu Thr Glu Val Glu Thr Tyr Val Leu
    130                 135                 140

Ser Leu Leu Thr Glu Val Glu Thr Tyr Val Leu Trp Leu Thr Gly Lys
145                 150                 155                 160

Asn Gly Leu Tyr Pro Trp Leu Thr Gly Lys Asn Gly Leu Tyr Pro Trp
                165                 170                 175

Leu Thr Gly Lys Asn Gly Leu Tyr Pro Trp Thr Gly Val Thr Gln Asn
            180                 185                 190

Pro Trp Thr Gly Val Thr Gln Asn Pro Trp Thr Gly Val Thr Gln Asn
        195                 200                 205

Pro Phe Trp Arg Gly Glu Asn Gly Arg Lys Thr Arg Ser Ala Tyr Glu
    210                 215                 220

Arg Met Cys Asn Ile Leu Lys Gly Lys Pro Phe Trp Arg Gly Glu Asn
225                 230                 235                 240

Gly Arg Lys Thr Arg Ser Ala Tyr Glu Arg Met Cys Asn Ile Leu Lys
                245                 250                 255

Gly Lys Pro Phe Trp Arg Gly Glu Asn Gly Arg Lys Thr Arg Ser Ala
            260                 265                 270

Tyr Glu Arg Met Cys Asn Ile Leu Lys Gly Lys Pro Pro Lys Tyr Val
        275                 280                 285

Lys Gln Asn Thr Leu Lys Leu Ala Thr Pro Pro Lys Tyr Val Lys Gln
    290                 295                 300

Asn Thr Leu Lys Leu Ala Thr Pro Pro Lys Tyr Val Lys Gln Asn Thr
305                 310                 315                 320

Leu Lys Leu Ala Thr Pro Ser Ala Ala Phe Glu Asp Leu Arg Val Leu
                325                 330                 335
```

Ser Phe Ile Arg Gly Tyr Pro Ser Ala Ala Phe Glu Asp Leu Arg Val
            340                 345                 350

Leu Ser Phe Ile Arg Gly Tyr Pro Ser Ala Ala Phe Glu Asp Leu Arg
        355                 360                 365

Val Leu Ser Phe Ile Arg Gly Tyr Pro Glu Leu Arg Ser Arg Tyr Trp
    370                 375                 380

Ala Ile Arg Thr Arg Ser Gly Pro Glu Leu Arg Ser Arg Tyr Trp Ala
385                 390                 395                 400

Ile Arg Thr Arg Ser Gly Pro Glu Leu Arg Ser Arg Tyr Trp Ala Ile
            405                 410                 415

Arg Thr Arg Ser Gly
            420

<210> SEQ ID NO 87
<211> LENGTH: 1335
<212> TYPE: DNA
<213> ORGANISM: Artificial
<220> FEATURE:
<223> OTHER INFORMATION: Synthetic polynucleotide

<400> SEQUENCE: 87

```
atgagatctc cggcgaaact gctgaaagaa cgtggctttt ttggcgcgat tgcgggcttt      60
ctggaaggca gcaaagcgta tagcaactgc tatccgtatg atgtgccgga ttacgcgagt     120
ctgggctctc tgctgaccga agtggaaacc tatgtgctgg gctggctgac cggcaaaaac     180
ggcctgtatc cggtgtggac cggcgtgacc cagaacggct tttggcgtgg cgaaaacggc     240
cgtaaaaccc gtagcgcgta tgaacgtatg tgcaacatcc tgaaaggcaa aggcccgaaa     300
tatgtgaaac agaacaccct gaaactggcc accggtgcga gcgcggcgtt tgaggacctg     360
cgtgttctga gctttattcg tggctatggc gaactgcgta ccgttattg gcgattcgt      420
acccgtagcg gtggtccgcc ggccaaactg ctgaaagaac gcggtttctt cggtgcgatc     480
gccggttttc tggaaggtag caaagcctac tctaattgtt acccgtacga tgttccggat     540
tacgccagcc tgggtagcct gctgaccgaa gttgaaacct acgttctggg ttggctgacc     600
ggtaaaaatg gtctgtaccc ggtttggacc ggtgttaccc agaatggttt ctggcgcggt     660
gaaaatggtc gcaaaacccg cagcgcctac gaacgcatgt gtaatattct gaaaggtaaa     720
ggtccgaaat acgttaaaca gaataccctg aaactggcca ccggcgccag cgccgccttc     780
gaggacctgc gcgttctgag cttcatccgc ggttacggtg aactgcgcag ccgctactgg     840
gccatccgca cccgcagcgg tggtccgccg gcgaaactgc tgaaagaacg cggtttttt      900
ggtgccattg cgggttttct ggaaggtagc aaagcctatt ctaactgcta tccgtacgat     960
gttccggatt atgcgagcct gggtagcctg ctgaccgaag tggaaaccta tgttctgggt    1020
tggctgaccg gcaaaaacgg tctgtatccg gtttggaccg gtgtgaccca gaacggtttt    1080
tggcgcggtg aaaacggccg taaaacccgc agcgcctatg aacgcatgtg caacattctg    1140
aaaggcaaag gtccgaaata cgtgaaacag aacaccctga aactggccac cggcgcgagc    1200
gcggcctttg aggacctgcg cgttctgagc tttattcgcg gctatggtga actgcgcagc    1260
cgctattggg cgattcgtac ccgcagcggc ggctaataac tcgagaagct ttctagacat    1320
atgatgcatg agctc                                                     1335
```

<210> SEQ ID NO 88
<211> LENGTH: 431
<212> TYPE: PRT
<213> ORGANISM: Artificial

<220> FEATURE:
<223> OTHER INFORMATION: Synthetic polypeptide

<400> SEQUENCE: 88

Met Arg Ser Pro Ala Lys Leu Leu Lys Glu Arg Gly Phe Phe Gly Ala
1               5                   10                  15

Ile Ala Gly Phe Leu Glu Gly Ser Lys Ala Tyr Ser Asn Cys Tyr Pro
                20                  25                  30

Tyr Asp Val Pro Asp Tyr Ala Ser Leu Gly Ser Leu Leu Thr Glu Val
            35                  40                  45

Glu Thr Tyr Val Leu Gly Trp Leu Thr Gly Lys Asn Gly Leu Tyr Pro
        50                  55                  60

Val Trp Thr Gly Val Thr Gln Asn Gly Phe Trp Arg Gly Glu Asn Gly
65              70                  75                  80

Arg Lys Thr Arg Ser Ala Tyr Glu Arg Met Cys Asn Ile Leu Lys Gly
                85                  90                  95

Lys Gly Pro Lys Tyr Val Lys Gln Asn Thr Leu Lys Leu Ala Thr Gly
                100                 105                 110

Ala Ser Ala Ala Phe Glu Asp Leu Arg Val Leu Ser Phe Ile Arg Gly
            115                 120                 125

Tyr Gly Glu Leu Arg Ser Arg Tyr Trp Ala Ile Arg Thr Arg Ser Gly
        130                 135                 140

Gly Pro Pro Ala Lys Leu Leu Lys Glu Arg Gly Phe Phe Gly Ala Ile
145                 150                 155                 160

Ala Gly Phe Leu Glu Gly Ser Lys Ala Tyr Ser Asn Cys Tyr Pro Tyr
                165                 170                 175

Asp Val Pro Asp Tyr Ala Ser Leu Gly Ser Leu Leu Thr Glu Val Glu
            180                 185                 190

Thr Tyr Val Leu Gly Trp Leu Thr Gly Lys Asn Gly Leu Tyr Pro Val
        195                 200                 205

Trp Thr Gly Val Thr Gln Asn Gly Phe Trp Arg Gly Glu Asn Gly Arg
    210                 215                 220

Lys Thr Arg Ser Ala Tyr Glu Arg Met Cys Asn Ile Leu Lys Gly Lys
225                 230                 235                 240

Gly Pro Lys Tyr Val Lys Gln Asn Thr Leu Lys Leu Ala Thr Gly Ala
                245                 250                 255

Ser Ala Ala Phe Glu Asp Leu Arg Val Leu Ser Phe Ile Arg Gly Tyr
            260                 265                 270

Gly Glu Leu Arg Ser Arg Tyr Trp Ala Ile Arg Thr Arg Ser Gly Gly
        275                 280                 285

Pro Pro Ala Lys Leu Leu Lys Glu Arg Gly Phe Phe Gly Ala Ile Ala
    290                 295                 300

Gly Phe Leu Glu Gly Ser Lys Ala Tyr Ser Asn Cys Tyr Pro Tyr Asp
305                 310                 315                 320

Val Pro Asp Tyr Ala Ser Leu Gly Ser Leu Leu Thr Glu Val Glu Thr
                325                 330                 335

Tyr Val Leu Gly Trp Leu Thr Gly Lys Asn Gly Leu Tyr Pro Val Trp
            340                 345                 350

Thr Gly Val Thr Gln Asn Gly Phe Trp Arg Gly Glu Asn Gly Arg Lys
        355                 360                 365

Thr Arg Ser Ala Tyr Glu Arg Met Cys Asn Ile Leu Lys Gly Lys Gly
    370                 375                 380

Pro Lys Tyr Val Lys Gln Asn Thr Leu Lys Leu Ala Thr Gly Ala Ser
385                 390                 395                 400

```
Ala Ala Phe Glu Asp Leu Arg Val Leu Ser Phe Ile Arg Gly Tyr Gly
            405                 410                 415

Glu Leu Arg Ser Arg Tyr Trp Ala Ile Arg Thr Arg Ser Gly Gly
            420                 425                 430

<210> SEQ ID NO 89
<211> LENGTH: 13
<212> TYPE: PRT
<213> ORGANISM: Artificial
<220> FEATURE:
<223> OTHER INFORMATION: Synthetic peptide

<400> SEQUENCE: 89

Pro Arg Tyr Val Lys Gln Asn Thr Leu Lys Leu Ala Thr
1               5                   10
```